(12) United States Patent
Yang et al.

(10) Patent No.: US 9,909,111 B2
(45) Date of Patent: *Mar. 6, 2018

(54) MUTANT LACTOBACILLUS BETA-GLUCURONIDASE ENZYMES WITH ENHANCED ENZYMATIC ACTIVITY

(71) Applicant: INTEGRATED MICRO-CHROMATOGRAPHY SYSTEMS, Columbia, SC (US)

(72) Inventors: Jia Yang, Columbia, SC (US); Gary Horvath, Columbia, SC (US); Pongkwan Sitasuwan, Columbia, SC (US); Margarita Marinova, Columbia, SC (US); Qian Wang, Columbia, SC (US); Lim Andrew Lee, Columbia, SC (US)

(73) Assignee: INTEGRATED MICRO-CHROMATOGRAPHY SYSTEMS, Irmo, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/076,183

(22) Filed: Mar. 21, 2016

(65) Prior Publication Data
US 2017/0267985 A1 Sep. 21, 2017

(51) Int. Cl.
*C12N 9/24* (2006.01)
*C12P 17/10* (2006.01)
*C12Q 1/40* (2006.01)

(52) U.S. Cl.
CPC ............ *C12N 9/2402* (2013.01); *C12P 17/10* (2013.01); *C12Q 1/40* (2013.01); *C12Y 302/01031* (2013.01); *G01N 2333/924* (2013.01)

(58) Field of Classification Search
None
See application file for complete search history.

(56) References Cited

U.S. PATENT DOCUMENTS

| | | | |
|---|---|---|---|
| 6,391,547 B1 | 5/2002 | Jefferson et al. | |
| 6,641,996 B1 | 11/2003 | Jefferson et al. | |
| 6,664,097 B2 | 12/2003 | Russell et al. | |
| 7,087,420 B1 | 8/2006 | Jefferson et al. | |
| 7,141,719 B2 | 11/2006 | Jefferson et al. | |
| 7,148,407 B2 | 12/2006 | Wenzl | |
| 7,176,006 B2 | 2/2007 | Jefferson et al. | |
| 8,491,891 B2 | 7/2013 | Roffler et al. | |
| 9,719,075 B2 | 8/2017 | Lee | |
| 2003/0003562 A1 | 1/2003 | Russell et al. | |
| 2003/0157684 A1 | 8/2003 | Jefferson et al. | |
| 2004/0091922 A1 | 5/2004 | Russell et al. | |
| 2005/0153448 A1 | 7/2005 | Wenzl | |
| 2005/0227306 A1* | 10/2005 | Fox | C12Q 1/37 435/23 |
| 2007/0037246 A1* | 2/2007 | Butt | C07K 14/00 435/69.1 |
| 2007/0081986 A1 | 4/2007 | Tomatsu et al. | |
| 2009/0041741 A1 | 2/2009 | Sly et al. | |
| 2010/0129367 A1 | 5/2010 | Roffler et al. | |
| 2013/0011381 A1 | 1/2013 | Sly et al. | |
| 2016/0090582 A1 | 3/2016 | Lee | |
| 2016/0237415 A1 | 8/2016 | Lee | |

FOREIGN PATENT DOCUMENTS

WO 00/55333 A1 9/2000
WO 2015/016124 A1 2/2015

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
U.S. Appl. No. 14/867,710, filed Jan. 12, 2017, R. Eckstrom.
U.S. Appl. No. 15/076,134, filed Apr. 3, 2017, R. Eckstrom.
U.S. Appl. No. 15/076,134, filed Dec. 2, 2016, R. Eckstrom.
Aich S. et al., "Expression and Purification of *Escherichia coli* beta-Glucuronidase," Protein Expression and Purification, vol. 22 (1), pp. 75-81, (2001).
Callanan, M.J. et al., "Modification of Lactobacillus beta-glucuronidase activity by random mutagenesis," Gene, vol. 389, pp. 122-127 (2007).
Chen, C. et al., "ECSTASY, an adjustable membrane-tethered/soluble protein expression system for the directed evolution of mammalian proteins," Protein Engineering, Design & Selection, vol. 25(7), pp. 367-375 (2012).
Flores, H. et al., "Increasing the thermal stability of an oligomeric protein, beta-glucuronidase.," J. Mol. Biol., vol. 315, Issue 3, pp. 325-337 (2002).
Fukao, M. et al., "Genomic Analysis by Deep Sequencing of the Probiotic Lactobacillus brevis KB290 Harboring Nine Plasmids Reveals Genomic Stability," PLOS ONE 8(3): e60521. doi:10.1371/journal.pone.0060521 (2013).
Geddie, M. et al., "Rapid Evolution of beta-Glucuronidase Specificity by Saturation Mutagenesis of an Active Site Loop," The Journal of Biological Chemistry, vol. 279(25) pp. 26462-26468 (2004).
Kim H.S. et al., "Cloning and expression of beta-glucuronidase from Lactobacillus brevis in *E. coli* and application in the bioconversion of baicalin and wogonoside," J Microbiol Biotechnol., vol. 19(12), pp. 1650-1655 (2009).

(Continued)

*Primary Examiner* — Richard G Hutson
(74) *Attorney, Agent, or Firm* — Nelson Mullins Riley & Scarborough LLP; Jill Gorny Sloper, Esq.

(57) ABSTRACT

Mutated *Lactobacillus brevis* strain 269Y β-glucuronidase enzymes with enhanced enzymatic activity at low pH (e.g., below pH 6.8), as well as enhanced thermostability as compared to wild type enzyme are provided. The enzymes of the invention advantageously allow for accurate analysis of bodily samples for the presence of drugs at low pH and in 30 minutes or less, as compared to the several hours needed using prior enzyme preparations. Methods of using the mutated enzymes for hydrolysis of glucuronide substrates, including opiates and benzodiazepines, are also provided.

24 Claims, 3 Drawing Sheets

(56) References Cited

OTHER PUBLICATIONS

Matsumura, I. et al., "Directed evolution of the surface chemistry of the reporter enzyme beta-glucuronidase," Nat. Biotechnol., vol. 17(7), pp. 696-701 (1999).
Matsumura, I., et al., "In vitro evolution of beta-glucuronidase into a beta-galactosidase proceeds through non-specific intermediates," J. Mol. Biol. vol. 305(2), pp. 331-339 (2001).
Morris, A. et al., "Opioid Hydrolysis by a Novel Recombinant Beta-Glucuronidase for Urinalysis," Ameritox Medication Monitoring Solutions, Poster Presentation, 2014, Society of Forensic Toxicologists Annual Meeting, held in Grand Rapids, Michigan, Oct. 19-24, 2014, 1 page.
Morris, A.A. et al., "Rapid Enzymatic Hydrolysis Using a Novel Recombinant beta-Glucuronidase in Benzodiazepine Urinalysis," Journal of Analytical Toxicology, vol. 38, pp. 610-614 (2014).
Morris, A.A. et al., "Rapid Enzyme Hydrolysis Using a Novel Recombinant beta-Glucuronidase in Benzodiazepine Urinalysis," Ameritox Medication Monitoring Solutions, Poster Presentation, 2014, American Association of Clinical Chemistry Annual Meeting in Chicago, Illinois, Jul. 30, 2014, 1 page.
Morris, A.A. et al., Buprenorphine Hydrolysis Using a Novel Recombinant Beta-glucuronidase for Urine Drug Testing, Ameritox Medication Monitoring Solutions, Poster Presentation, 2014, Society of Forensic Toxicologists Annual Meeting, held in Grand Rapids, Michigan, Oct. 19-24, 2014, 1 page.
Russell W.M., et al., "Identification and cloning of gusA, Encoding a New Beta-Glucuronidase from Lactobacillus Gasseri ADH," Applied and Environmental Microbiology, vol. 67(3), pp. 1253-1261 (2001).
Sakurama, H. et al., "Beta-Glucuronidase from Lactobacillus brevis useful for baicalin hydrolysis belongs to glycoside hydrolase family 30," Appl Microbiol Biotechnol., vol. 98:4021-4032 (2014).
Xiong, A.S. et al., "Directed evolution of a beta-galactosidase from Pyrococcus woesei resulting in increased thermostable beta-glucuronidase activity," Appl Microbial Biotechnoly, vol. 77(3), pp. 569-578 (2007).
Xiong, A., et al. "Concurrent mutations in six amino acids in beta-glucuronidase improve its thermostability," Protein Engineering, Design & Selection, vol. 20(7) pp. 319-325 (2007).
U.S. Appl. No. 15/076,134, filed Mar. 21, 2016, Lim Andrew Lee.
U.S. Appl. No. 14/867,710, filed Sep. 28, 2015, Lim Andrew Lee.
U.S. Appl. No. 15/076,134, filed Jul. 27, 2016, R. Eckstrom.
U.S. Appl. No. 14/867,710, filed Jul. 27, 2016, R. Eckstrom.
GenBank Accession No. WP 015255760.1, published May 28, 2013.
Genseq Accession No. AAW93825, published Jun. 15, 2007.
Hernandez et al., "Control of protein immobilization: Coupling immobilization and site-directed mutagenesis to improve biocatalyst or biosensor performance," Enzyme and Microbial Technology, vol. 48:107-122 (2011).
PIR Accession No. A25047, published Jun. 30, 1988.
PIR Accession No. A72300, published Jun. 11, 1999.
U.S. Appl. No. 14/867,710, filed Aug. 16, 2017, R. Eckstrom.

* cited by examiner

```
Lb269Y   1  MLYPMETASR VVLDLSGVWR FMIDKEQIPV DVTRPLPATL SMAVPASFND QTASKEIREH   60
LbR01    1  MLYPMETASR VVLDLSGVWR FMIDKEQIPV DVTRPLPATL SMAVPASFND QTASKEIREH   60

Lb269Y  61  VGYVWYERC FELPQLLRQER LVLRPGSATH EAWVYLNGHL ITHHKGGFTP FEVEINDDLV   120
LbR01   61  VGYVWYERC FELPQLLRQER LVLRPGSATH EAWVYLNGHL ITHHKGGFTP FEVEINDDLV   120

Lb269Y 121  TGENRLTVK LSNMLDYTTLP VGHYKETQNE TGQRVRQLDE NFDFFNYAGL QRFVKIYSTP   180
LbR01  121  TGENRLTVK LSNMLDYTTLP VGHYKETQNE TGQRVRQLDE NFDFFNYAGL QRFVKIYSTP   180

Lb269Y 181  HSYIRDITL TPKVNLTNHSA VVNGEIETVG DVEQVVVTIL DEDNQIVGTT SGKTLAIELN   240
LbR01  181  HSYIRDITL TPKVNLTNHSA VVNGEIETVG DVEQVVVTIL DEDNQIVGTT SGKTLAIELN   240

Lb269Y 241  SVHLMQPGK AYLYRAKVELY QAGQVIDTYI EAFGIRQIAV KAGKFLINGQ PFYFKGFGKH   300
LbR01  241  SVHLNQPGK AYLYRAKVELY QAGQVIDTYI ETFGIRQIAV KAGKFLINGQ PFYFKGFGKH   300

Lb269Y 301  EDAYIHGRG LSEPQNVLDLS LMKQMGANSF RTSHYPYSEE MMRLCDREGI VVIDEVPAVG   360
LbR01  301  EDAYIHGRG LSEPQNVLDLS LMKQMGANSF RTSHYPYSEE MMRLCDREGI VVIDEVPAVG   360

Lb269Y 361  LMLSFTFDV SALEKDDFEDD TWEKLRTAEA HRQAITEMID RDKNHASVVM WSISNEAANF   420
LbR01  361  LMLSFTFDV SALEKDDFEDD TWEKLRTAEA HRQAITEMID RDKNHASVVM WSISNEAANF   420

Lb269Y 421  SKGAYEYFK PLFDLARKLDP QQRPCTYTSI MMTTLKTDRC LALADVIALN RYYGWYMGNG   480
LbR01  421  SKGAYEYFK PLFDLARKLDP QQRPCTSTSI MMTTLKTDRC LALADVIALN RYYGWYMGNG   480

Lb269Y 481  DLKAAETAT REELLAYQAKF PDKPIMYTEY GADTIAGLHS NYDEPFSEEF QSDYYRMCSR   540
LbR01  481  DLKAASTAT REELLAYQAKF PDKPIMYTEY GADTIAGLHS NYDEPFSEEF QEDYYRMCSR   540

Lb269Y 541  VFDEVINFV GEQLWNFADFQ TKFGIQRMQG NKKGIFTRAR EPKMVVRYLT QRWRNIPDFN   600
LbR01  541  VFDEVTNFV GEQLWNFADFQ TKFGIQRGQG NKKGIFTRAR EPKMVVRYLT QRWRNIPDFN   600

Lb269Y 601  YKK  603
LbR01  601  YKK  603
```

FIGURE 1

```
LbGUS    MLYPMETASRVVLDLSGVWRFMIDREQIPVDVTRPLPATLSMAVPASFNDQTASKEIREHVGYVWYERCFEL
Lb1F     MLYPMETASRVVLDLSGVWRFMIDREQIPVDVTRPLPATLSMAVPASFNDQTASKEIREHVGYVWYERCFEL
Lb-1C    MLYPMETASRVVLDLSGVWRFMIDREQIPVDVTRPLPATLSMAVPASFNDQTASKEIREHVGYVWYERCFEL
Lb1F-1C  MLYPMETASRVVLDLSGVWRFMIDREQIPVDVTRPLPATLSMAVPASFNDQTASKEIREHVGYVWYERCFEL

LbGUS    PQLLRQERLVLRFGSATHEAWVYLNGHLITHEKGGFTPFEVEINDDLVTGENRLTVKLSNMLDYTTLPVGHY
Lb1F     PQLLRQERLVLRFGSATHEAWVYLNGHLITHEKGGFTPFEVEINDDLVTGENRLTVKLSNMLDYTTLPVGHY
Lb-1C    PQLLRQERLVLRFGSATHEAWVYLNGHLITHEKGGFTPFEVEINDDLVTGENRLTVKLSNMLDYTTLPVGHY
Lb1F-1C  PQLLRQERLVLRFGSATHEAWVYLNGHLITHEKGGFTPFEVEINDDLVTGENRLTVKLSNMLDYTTLPVGHY

LbGUS    KETQNETGQRVRQLDENFDFFNYAGLQRPVKIYSTPHSYIRDITLTPKVNLTNHSAVVNGEIETVGDVEQVV
Lb1F     KETQNETGQRVRQLDENFDFFNYAGLQRPVKIYSTPHSYIRDITLTPKVNLTNHSAVVNGEIETVGDVEQVV
Lb-1C    KETQNETGQRVRQLDENFDFFNYAGLQRPVKIYSTPHSYIRDITLTPKVNLTNHSAVVNGEIETVGDVEQVV
Lb1F-1C  KETQNETGQRVRQLDENFDFFNYAGLQRPVKIYSTPHSYIRDITLTPKVNLTNHSAVVNGEIETVGDVEQVV

LbGUS    VTILDEDNQIVGTTSGKTLAIELNSVHLWQPGKAYLYRAKVELYQAGQVIDTYIEAFGIRQIAVKAGKFLIN
Lb1F     VTILDEDNQIVGTTSGKTLAIELNSVHLWQPGKAYLYRAKVELYQAGQVIDTYIEAFGIRQIAVKAGKFLIN
Lb-1C    VTILDEDNQIVGTTSGKTLAIELNSVHLWQPGKAYLYRAKVELYQAGQVIDTYIEAFGIRQIAVKAGKFLIN
Lb1F-1C  VTILDEDNQIVGTTSGKTLAIELNSVHLWQPGKAYLYRAKVELYQAGQVIDTYIEAFGIRQIAVKAGKFLIN

LbGUS    GQPFYFKGFGKHEDAYIHGPGLSEPQNVLDLSLMKQMGANSFRTSHYPYSEEMMRLCDREGIVVIDEVPAVG
Lb1F     GQPFYFKGFGKHEDAYIHGRGLSEPQNVLDLSLMKQMGANSFRTSHYPYSEEMMRLCDREGIVVIDEVPAVG
Lb-1C    GQPFYFKGFGKHEDAYIHGRGLSEPQNVLDLSLMKQMGANSFRTSHYPYSEEMMRLCDREGIVVIDEVPAVG
Lb1F-1C  GQPFYFKGFGKHEDAYIHGRGLSEPQNVLDLSLMKQMGANSFRTSHYPYSEEMMRLCDREGIVVIDEVPAVG

LbGUS    LMLSPTFDVSALEKDDFEDDTWEKLRTAEAHRQAITEMIDRDKNHASVVMWSISNEAANFSKGAYEYFKPLF
Lb1F     LMLSPTFDVSALEKDDFEDDTWEKLRTAEAHRQAITEMIDRDKNHASVVMWSISNEAANFSKGAYEYFKPLF
Lb-1C    LMLSPTFDVSALEKDDFEDDTWEKLRTAEAHRQAITEMIDRDKNHASVVMWSISNEAANFSKGAYEYFKPLF
Lb1F-1C  LMLSPTFDVSALEKDDFEDDTWEKLRTAEAHRQAITEMIDRDKNHASVVMWSISNEAANFSKGAYEYFKPLF

LbGUS    DLARKLDPQQRPCTYTSIMMTTLKTDRCLALADVIALNRYYGWYMGNGDLKAAETATREELLAYQAKFPDKP
Lb1F     DLARKLDPQQRPCTYTSIMMTTLKTDRCLALADVIALNRYYGWYMGNGDLKAAETATREELLAYQAKFPDKP
Lb-1C    DLARKLDPQQRPCTYTSIMMTTLKTDRCLALADVIALNRYYGWYMGNGDLKAAETATREELLAYQAKFPDKP
Lb1F-1C  DLARKLDPQQRPCTYTSIMMTTLKTDRCLALADVIALNRYYGWYMGNGDLKAAETATREELLAYQAKFPDKP

LbGUS    IMYTEYGADTIAGLHSNYDEPFSEEFQEDYYRMCSRVFDEVTNFVGEQLWNFADFQTKF*GI*QRVQGNKKGIF
Lb1F     IMYTEYGADTIAGLHSNYDEPFSEEFQEDYYRMCSRVFDEVTNFVGEQLWNFADFQTKF*SI*QRVQGNKKGIF
Lb-1C    IMYTEYGADTIAGLHSNYDEPFSEEFQEDYYRMCSRVFDEVTNFVGEQLWNFADFQTKF*GI*QRVQGNKKGIF
Lb1F-1C  IMYTEYGADTIAGLHSNYDEPFSEEFQEDYYRMCSRVFDEVTNFVGEQLWNFADFQTKF*SI*QRVQGNKKGIF

LbGUS    TRAREPKMVVRYLTQRWRNIPDFNYKK-
Lb1F     TRAREPKMVVRYLTQRWRNIPDFNYKK-
Lb-1C    TRAREPKMVVRYLTQRWRNIPDFNYKK*C*
Lb1F-1C  TRAREPKMVVRYLTQRWRNIPDFNYKK*C*
```

FIGURE 2

SEQUENCE LISTING

<160> NUMBER OF SEQ ID NOS: 17

<210> SEQ ID NO 1
<211> LENGTH: 1812
<212> TYPE: DNA
<213> ORGANISM: Lactobacillus brevis

<400> SEQUENCE: 1

```
atgttatatc caatggaaac agcgtcacga gtggttttag atttatcagg tgtctggcgg      60
tttatgattg ataaagaaca gataccagtt gatgtgactc gtccgttgcc ggcaacctta     120
tcgatggcag ttccagcttc atttaacgat cagacggcat caaaagagat ccgtgaacat     180
gtcggatacg tttggtatga acggtgtttt gagctgcccc aattactgcg gcaagaaaga     240
ctcgttttgc ggtttggctc cgcaacgcat gaggcctggg tgtatcttaa tggccactta     300
atcacgcatc acaagggtgg ctttacaccg tttgaagtag aaattaatga cgacttagtg     360
actggtgaga atcgactgac ggttaaactt agtaatatgc ttgactatac aactttgccg     420
gtcggacatt acaaagaaac gcaaaatgag acgggccaac gggtacggca attagatgaa     480
aattttgact tcttttaatta tgcggggtta cagcgtcctg taaaaatcta cagtacgcca     540
cacagctata ttcgagacat tacgttgacg cctaaggtta atttgaccaa tcactcggcg     600
gtggttaatg gtgaaattga cggtaggc gatgttgaac aggtagtcgt cacgatctta     660
gacgaagata accagattgt tggtaccacg agtgggaaaa cactggcaat tgagttgaac     720
tcagttcatc tatggcagcc gggaaaggcc tacctgtatc gcgctaaagt agaattgtat     780
caggcggggc aagtgattga tacgtacatc gaggcgtttg gcattcggca aattgcggtc     840
aaggctggta aattttttgat taacgggcag cccttttact tcaaaggatt tgggaaacac     900
gaagacgctt atattcatgg tcgagggtta agcgaaccac agaatgtctt ggatttgagc     960
ctaatgaagc agatgggggc taattcattc cgaacgtccc attacccgta ttcagaagaa    1020
atgatgcggc tatgtgatcg tgaggggatc gttgtgattg atgaggtgcc ggcagttgga    1080
ttgatgctgt cctttacctt tgatgtttcg gcactagaaa aggatgattt tgaagacgat    1140
acgtgggaaa aattacggac ggctgaggcc catcgtcagg cgatcactga gatgattgat    1200
cgtgataaaa atcatgcctc agtggtgatg tggtcaatct ctaatgaggc cgccaacttt    1260 tccaagggg cctatgagta ctttaagccg ttatttgatc tggctcgcaa gctggatcca    1320
cagcaacgac catgcacgta taccagtatt atgatgacaa cgttaaaaac agatcggtgt    1380
ttggcactag ccgatgtgat tgcgctgaac cgatactatg gttggtatat gggcaatggt    1440
gatttgaaag cagcagaaac tgcgacgcgc gaagaacttt tagcttatca ggcaaagttc    1500
```

-continued

```
ccagacaagc caatcatgta taccgaatat ggtgcggata cgattgcggg gttgcatagt    1560
aattacgatg agccgttttc cgaagagttc caagaagatt actatcggat gtgtagtcgg    1620 gttttttgatg aagtgactaa ctttgttggc gagcaacttt ggaattttgc tgatttccaa    1680
acaaaatttg ggattcaacg cgttcaagga aataagaagg ggattttttac ccgagcgcgt    1740 gaacccaaaa tggtggttcg gtatttaaca caacggtggc ggaatattcc ggactttaat    1800
tataaaaaat ag                                                         1812
```

<210> SEQ ID NO 2
<211> LENGTH: 603
<212> TYPE: PRT
<213> ORGANISM: Lactobacillus brevis

<400> SEQUENCE: 2

```
Met Leu Tyr Pro Met Glu Thr Ala Ser Arg Val Val Leu Asp Leu Ser
1               5                   10                  15

Gly Val Trp Arg Phe Met Ile Asp Lys Glu Gln Ile Pro Val Asp Val
            20                  25                  30

Thr Arg Pro Leu Pro Ala Thr Leu Ser Met Ala Val Pro Ala Ser Phe
        35                  40                  45

Asn Asp Gln Thr Ala Ser Lys Glu Ile Arg Glu His Val Gly Tyr Val
    50                  55                  60

Trp Tyr Glu Arg Cys Phe Glu Leu Pro Gln Leu Arg Gln Glu Arg
65                  70                  75                  80

Leu Val Leu Arg Phe Gly Ser Ala Thr His Glu Ala Trp Val Tyr Leu
                85                  90                  95

Asn Gly His Leu Ile Thr His His Lys Gly Gly Phe Thr Pro Phe Glu
            100                 105                 110

Val Glu Ile Asn Asp Asp Leu Val Thr Gly Glu Asn Arg Leu Thr Val
        115                 120                 125

Lys Leu Ser Asn Met Leu Asp Tyr Thr Thr Leu Pro Val Gly His Tyr
    130                 135                 140

Lys Glu Thr Gln Asn Glu Thr Gly Gln Arg Val Arg Gln Leu Asp Glu
145                 150                 155                 160

Asn Phe Asp Phe Phe Asn Tyr Ala Gly Leu Gln Arg Pro Val Lys Ile
                165                 170                 175

Tyr Ser Thr Pro His Ser Tyr Ile Arg Asp Ile Thr Leu Thr Pro Lys
            180                 185                 190

Val Asn Leu Thr Asn His Ser Ala Val Val Asn Gly Glu Ile Glu Thr
        195                 200                 205

Val Gly Asp Val Glu Gln Val Val Val Thr Ile Leu Asp Glu Asp Asn
    210                 215                 220

Gln Ile Val Gly Thr Thr Ser Gly Lys Thr Leu Ala Ile Glu Leu Asn
225                 230                 235                 240

Ser Val His Leu Trp Gln Pro Gly Lys Ala Tyr Leu Tyr Arg Ala Lys
                245                 250                 255

Val Glu Leu Tyr Gln Ala Gly Gln Val Ile Asp Thr Tyr Ile Glu Ala
            260                 265                 270

Phe Gly Ile Arg Gln Ile Ala Val Lys Ala Gly Lys Phe Leu Ile Asn
        275                 280                 285

Gly Gln Pro Phe Tyr Phe Lys Gly Phe Gly Lys His Glu Asp Ala Tyr
    290                 295                 300

Ile His Gly Arg Gly Leu Ser Glu Pro Gln Asn Val Leu Asp Leu Ser
```

```
            305                 310                 315                 320
Leu Met Lys Gln Met Gly Ala Asn Ser Phe Arg Thr Ser His Tyr Pro
                325                 330                 335

Tyr Ser Glu Glu Met Met Arg Leu Cys Asp Arg Glu Gly Ile Val Val
                340                 345                 350

Ile Asp Glu Val Pro Ala Val Gly Leu Met Leu Ser Phe Thr Phe Asp
                355                 360                 365

Val Ser Ala Leu Glu Lys Asp Asp Phe Glu Asp Thr Trp Glu Lys
            370                 375                 380

Leu Arg Thr Ala Glu Ala His Arg Gln Ala Ile Thr Glu Met Ile Asp
385                 390                 395                 400

Arg Asp Lys Asn His Ala Ser Val Val Met Trp Ser Ile Ser Asn Glu
                405                 410                 415

Ala Ala Asn Phe Ser Lys Gly Ala Tyr Glu Tyr Phe Lys Pro Leu Phe
                420                 425                 430

Asp Leu Ala Arg Lys Leu Asp Pro Gln Gln Arg Pro Cys Thr Tyr Thr
                435                 440                 445

Ser Ile Met Met Thr Thr Leu Lys Thr Asp Arg Cys Leu Ala Leu Ala
            450                 455                 460

Asp Val Ile Ala Leu Asn Arg Tyr Tyr Gly Trp Tyr Met Gly Asn Gly
465                 470                 475                 480

Asp Leu Lys Ala Ala Glu Thr Ala Thr Arg Glu Glu Leu Leu Ala Tyr
                485                 490                 495

Gln Ala Lys Phe Pro Asp Lys Pro Ile Met Tyr Thr Glu Tyr Gly Ala
                500                 505                 510

Asp Thr Ile Ala Gly Leu His Ser Asn Tyr Asp Glu Pro Phe Ser Glu
                515                 520                 525

Glu Phe Gln Glu Asp Tyr Tyr Arg Met Cys Ser Arg Val Phe Asp Glu
                530                 535                 540

Val Thr Asn Phe Val Gly Glu Gln Leu Trp Asn Phe Ala Asp Phe Gln
545                 550                 555                 560

Thr Lys Phe Gly Ile Gln Arg Val Gln Gly Asn Lys Lys Gly Ile Phe
                565                 570                 575

Thr Arg Ala Arg Glu Pro Lys Met Val Val Arg Tyr Leu Thr Gln Arg
                580                 585                 590

Trp Arg Asn Ile Pro Asp Phe Asn Tyr Lys Lys
                595                 600

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagagacata tgttatatcc aatggaaaca g                                     31

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```
gagagaaagc ttctattttt tataattaaa gtccggaata ttc    43

<210> SEQ ID NO 5
<211> LENGTH: 603
<212> TYPE: PRT
<213> ORGANISM: Lactobacillus brevis

<400> SEQUENCE: 5

Met Leu Tyr Pro Met Glu Thr Ala Ser Arg Val Val Leu Asp Leu Ser
1               5                   10                  15

Gly Val Trp Arg Phe Met Ile Asp Lys Glu Gln Ile Pro Val Asp Val
                20                  25                  30

Thr Arg Pro Leu Pro Ala Thr Leu Ser Met Ala Val Pro Ala Ser Phe
            35                  40                  45

Asn Asp Gln Thr Ala Ser Lys Glu Ile Arg Glu His Val Gly Tyr Val
        50                  55                  60

Trp Tyr Glu Arg Cys Phe Glu Leu Pro Gln Leu Leu Arg Gln Glu Arg
65                  70                  75                  80

Leu Val Leu Arg Phe Gly Ser Ala Thr His Glu Ala Trp Val Tyr Leu
                85                  90                  95

Asn Gly His Leu Ile Thr His His Lys Gly Gly Phe Thr Pro Phe Glu
            100                 105                 110

Val Glu Ile Asn Asp Asp Leu Val Thr Gly Glu Asn Arg Leu Thr Val
        115                 120                 125

Lys Leu Ser Asn Met Leu Asp Tyr Thr Thr Leu Pro Val Gly His Tyr
    130                 135                 140

Lys Glu Thr Gln Asn Glu Thr Gly Gln Arg Val Arg Gln Leu Asp Glu
145                 150                 155                 160

Asn Phe Asp Phe Phe Asn Tyr Ala Gly Leu Gln Arg Pro Val Lys Ile
                165                 170                 175

Tyr Ser Thr Pro His Ser Tyr Ile Arg Asp Ile Thr Leu Thr Pro Lys
            180                 185                 190

Val Asn Leu Thr Asn His Ser Ala Val Val Asn Gly Glu Ile Glu Thr
        195                 200                 205

Val Gly Asp Val Glu Gln Val Val Thr Ile Leu Asp Glu Asp Asn
    210                 215                 220

Gln Val Val Gly Thr Thr Ser Gly Lys Thr Leu Ala Ile Glu Leu Asn
225                 230                 235                 240

Ser Val His Leu Trp Gln Pro Gly Lys Ala Tyr Leu Tyr Arg Ala Lys
                245                 250                 255

Val Glu Leu Tyr Gln Ala Gly Gln Val Ile Asp Thr Tyr Ile Glu Thr
            260                 265                 270

Phe Gly Ile Arg Gln Ile Ala Val Lys Ala Gly Lys Phe Leu Ile Asn
        275                 280                 285

Gly Gln Pro Phe Tyr Phe Lys Gly Phe Gly Lys His Glu Asp Ala Tyr
    290                 295                 300

Ile His Gly Arg Gly Leu Ser Glu Pro Gln Asn Val Leu Asp Leu Ser
305                 310                 315                 320

Leu Met Lys Gln Met Gly Ala Asn Ser Phe Arg Thr Ser His Tyr Pro
                325                 330                 335

Tyr Ser Glu Glu Met Met Arg Leu Cys Asp Arg Glu Gly Ile Val Val
            340                 345                 350

Ile Asp Glu Val Pro Ala Val Gly Leu Met Leu Ser Phe Thr Phe Asp
        355                 360                 365

```
Val Ser Ala Leu Glu Lys Asp Asp Phe Glu Asp Thr Trp Glu Lys
    370                 375                 380

Leu Arg Thr Ala Glu Ala His Arg Gln Ala Ile Thr Glu Met Ile Asp
385                 390                 395                 400

Arg Asp Lys Asn His Ala Ser Val Val Met Trp Ser Ile Ser Asn Glu
                405                 410                 415

Ala Ala Asn Phe Ser Lys Gly Ala Tyr Glu Tyr Phe Lys Pro Leu Phe
                420                 425                 430

Asp Leu Ala Arg Lys Leu Asp Pro Gln Gln Arg Pro Cys Thr Ser Thr
                435                 440                 445

Ser Ile Met Met Thr Thr Leu Lys Thr Asp Arg Cys Leu Ala Leu Ala
    450                 455                 460

Asp Val Ile Ala Leu Asn Arg Tyr Tyr Gly Trp Tyr Met Gly Asn Gly
465                 470                 475                 480

Asp Leu Lys Ala Ala Glu Thr Ala Thr Arg Glu Glu Leu Leu Ala Tyr
                485                 490                 495

Gln Ala Lys Phe Pro Asp Lys Pro Ile Met Tyr Thr Glu Tyr Gly Ala
                500                 505                 510

Asp Thr Ile Ala Gly Leu His Ser Asn Tyr Asp Glu Pro Phe Ser Glu
    515                 520                 525

Glu Phe Gln Glu Asp Tyr Tyr Arg Met Cys Ser Arg Val Phe Asp Glu
    530                 535                 540

Val Thr Asn Phe Val Gly Glu Gln Leu Trp Asn Phe Ala Asp Phe Gln
545                 550                 555                 560

Thr Lys Phe Gly Ile Gln Arg Gly Gln Gly Asn Lys Lys Gly Ile Phe
                565                 570                 575

Thr Arg Ala Arg Glu Pro Lys Met Val Val Arg Tyr Leu Thr Gln Arg
                580                 585                 590

Trp Arg Asn Ile Pro Asp Phe Asn Tyr Lys Lys
    595                 600

<210> SEQ ID NO 6
<211> LENGTH: 1812
<212> TYPE: DNA
<213> ORGANISM: Lactobacillus brevis

<400> SEQUENCE: 6
atgttatatc caatggaaac agcgtcacga gtggttttag atttatcagg tgtctggcgg      60
tttatgattg ataaagaaca gataccagtt gatgtgactc gtccgttgcc ggcaaccttt     120
tcgatggcag ttccagcttc atttaacgat cagacggcat caaaagagat ccgtgaacat     180
gtcggatacg tttggtatga acggtgtttt gagctgcccc aattactgcg gcaagaaaga     240
ctcgttttgc ggtttggctc cgcaacgcat gaggcctggg tgtatcttaa tggccactta     300
atcacgcatc acaagggtgg ctttacaccg tttgaagtag aaattaatga cgacttagtg     360
actggtgaga atcgactgac ggttaaactt agtaatatgc ttgactatac aactttgccg     420
gtcggacatt acaaagaaac gcaaaatgag acgggccaac gggtacggca attagatgaa     480
aattttgact tctttaatta tgcggggtta cagcgtcctg taaaaatcta cagtacgcca     540
cacagctata ttcgagacat tacgttgacg cctaaggtta atttgaccaa tcactcggcg     600
gtggttaatg gtgaaattga acggtaggc gatgttgaac aggtagtcgt cacgatctta     660
gacgaagata accagattgt tggtaccacg agtgggaaaa cactggcaat tgagttgaac     720
tcagttcatc tatggcagcc gggaaaggcc tacctgtatc gcgctaaagt agaattgtat     780
```

-continued

```
caggcggggc aagtgattga tacgtacatc gaggcgtttg gcattcggca aattgcggtc    840
aaggctggta aattttttgat taacgggcag ccctttttact tcaaaggatt tgggaaacac   900
gaagacgctt atattcatgg tcgagggtta agcgaaccac agaatgtctt ggatttgagc    960
ctaatgaagc agatggggc taattcattc gaacgtccc attacccgta ttcagaagaa    1020
atgatgcggc tatgtgatcg tgaggggatc gttgtgattg atgaggtgcc ggcagttgga   1080
ttgatgctgt cctttacctt tgatgtttcg gcactagaaa aggatgattt tgaagacgat   1140
acgtgggaaa aattacggac ggctgaggcc catcgtcagg cgatcactga gatgattgat   1200
cgtgataaaa atcatgcctc agtggtgatg tggtcaatct ctaatgaggc cgccaacttt   1260 tccaagggg cctatgagta ctttaagccg ttatttgatc tggctcgcaa gctggatcca   1320
cagcaacgac catgcacgta taccagtatt atgatgacaa cgttaaaaac agatcggtgt   1380
ttggcactag ccgatgtgat tgcgctgaac cgatactatg gttggtatat gggcaatggt   1440
gatttgaaag cagcagaaac tgcgacgcgc gaagaacttt tagcttatca ggcaaagttc   1500
ccagacaagc caatcatgta taccgaatat ggtgcggata cgattgcggg gttgcatagt   1560
aattacgatg agccgttttc cgaagagttc caagaagatt actatcggat gtgtagtcgg   1620 gttttttgatg aagtgactaa ctttgttggc gagcaacttt ggaattttgc tgatttccaa   1680
acaaaattta gcattcaacg cgttcaagga aataagaagg ggattttttac ccgagcgcgt   1740 gaacccaaaa tggtggttcg gtatttaaca caacggtggc ggaatattcc ggactttaat   1800
tataaaaaat ag                                                       1812
```

<210> SEQ ID NO 7
<211> LENGTH: 603
<212> TYPE: PRT
<213> ORGANISM: Lactobacillus brevis

<400> SEQUENCE: 7

```
Met Leu Tyr Pro Met Glu Thr Ala Ser Arg Val Val Leu Asp Leu Ser
1               5                   10                  15

Gly Val Trp Arg Phe Met Ile Asp Lys Glu Gln Ile Pro Val Asp Val
            20                  25                  30

Thr Arg Pro Leu Pro Ala Thr Leu Ser Met Ala Val Pro Ala Ser Phe
        35                  40                  45

Asn Asp Gln Thr Ala Ser Lys Glu Ile Arg Glu His Val Gly Tyr Val
    50                  55                  60

Trp Tyr Glu Arg Cys Phe Glu Leu Pro Gln Leu Leu Arg Gln Glu Arg
65                  70                  75                  80

Leu Val Leu Arg Phe Gly Ser Ala Thr His Glu Ala Trp Val Tyr Leu
                85                  90                  95

Asn Gly His Leu Ile Thr His His Lys Gly Gly Phe Thr Pro Phe Glu
            100                 105                 110

Val Glu Ile Asn Asp Asp Leu Val Thr Gly Glu Asn Arg Leu Thr Val
        115                 120                 125

Lys Leu Ser Asn Met Leu Asp Tyr Thr Thr Leu Pro Val Gly His Tyr
    130                 135                 140

Lys Glu Thr Gln Asn Glu Thr Gly Gln Arg Val Arg Gln Leu Asp Glu
145                 150                 155                 160

Asn Phe Asp Phe Phe Asn Tyr Ala Gly Leu Gln Arg Pro Val Lys Ile
                165                 170                 175

Tyr Ser Thr Pro His Ser Tyr Ile Arg Asp Ile Thr Leu Thr Pro Lys
```

```
                180                 185                 190
Val Asn Leu Thr Asn His Ser Ala Val Val Asn Gly Glu Ile Glu Thr
            195                 200                 205
Val Gly Asp Val Glu Gln Val Val Thr Ile Leu Asp Glu Asp Asn
        210                 215                 220
Gln Ile Val Gly Thr Thr Ser Gly Lys Thr Leu Ala Ile Glu Leu Asn
225                 230                 235                 240
Ser Val His Leu Trp Gln Pro Gly Lys Ala Tyr Leu Tyr Arg Ala Lys
                245                 250                 255
Val Glu Leu Tyr Gln Ala Gly Gln Val Ile Asp Thr Tyr Ile Glu Ala
            260                 265                 270
Phe Gly Ile Arg Gln Ile Ala Val Lys Ala Gly Lys Phe Leu Ile Asn
        275                 280                 285
Gly Gln Pro Phe Tyr Phe Lys Gly Phe Gly Lys His Glu Asp Ala Tyr
    290                 295                 300
Ile His Gly Arg Gly Leu Ser Glu Pro Gln Asn Val Leu Asp Leu Ser
305                 310                 315                 320
Leu Met Lys Gln Met Gly Ala Asn Ser Phe Arg Thr Ser His Tyr Pro
                325                 330                 335
Tyr Ser Glu Glu Met Met Arg Leu Cys Asp Arg Glu Gly Ile Val Val
            340                 345                 350
Ile Asp Glu Val Pro Ala Val Gly Leu Met Leu Ser Phe Thr Phe Asp
        355                 360                 365
Val Ser Ala Leu Glu Lys Asp Asp Phe Glu Asp Thr Trp Glu Lys
    370                 375                 380
Leu Arg Thr Ala Glu Ala His Arg Gln Ala Ile Thr Glu Met Ile Asp
385                 390                 395                 400
Arg Asp Lys Asn His Ala Ser Val Val Met Trp Ser Ile Ser Asn Glu
                405                 410                 415
Ala Ala Asn Phe Ser Lys Gly Ala Tyr Glu Tyr Phe Lys Pro Leu Phe
            420                 425                 430
Asp Leu Ala Arg Lys Leu Asp Pro Gln Gln Arg Pro Cys Thr Tyr Thr
        435                 440                 445
Ser Ile Met Met Thr Thr Leu Lys Thr Asp Arg Cys Leu Ala Leu Ala
    450                 455                 460
Asp Val Ile Ala Leu Asn Arg Tyr Tyr Gly Trp Tyr Met Gly Asn Gly
465                 470                 475                 480
Asp Leu Lys Ala Ala Glu Thr Ala Thr Arg Glu Glu Leu Leu Ala Tyr
                485                 490                 495
Gln Ala Lys Phe Pro Asp Lys Pro Ile Met Tyr Thr Glu Tyr Gly Ala
            500                 505                 510
Asp Thr Ile Ala Gly Leu His Ser Asn Tyr Asp Glu Pro Phe Ser Glu
        515                 520                 525
Glu Phe Gln Glu Asp Tyr Tyr Arg Met Cys Ser Arg Val Phe Asp Glu
    530                 535                 540
Val Thr Asn Phe Val Gly Glu Gln Leu Trp Asn Phe Ala Asp Phe Gln
545                 550                 555                 560
Thr Lys Phe Ser Ile Gln Arg Val Gln Gly Asn Lys Lys Gly Ile Phe
                565                 570                 575
Thr Arg Ala Arg Glu Pro Lys Met Val Val Arg Tyr Leu Thr Gln Arg
            580                 585                 590
Trp Arg Asn Ile Pro Asp Phe Asn Tyr Lys Lys
        595                 600
```

<210> SEQ ID NO 8
<211> LENGTH: 1815
<212> TYPE: DNA
<213> ORGANISM: Lactobacillus brevis

<400> SEQUENCE: 8

| | | | | | | |
|---|---|---|---|---|---|---|
| atgttatatc | caatggaaac | agcgtcacga | gtggttttag | atttatcagg | tgtctggcgg | 60 |
| tttatgattg | ataaagaaca | gataccagtt | gatgtgactc | gtccgttgcc | ggcaacctta | 120 |
| tcgatggcag | ttccagcttc | atttaacgat | cagacggcat | caaaagagat | ccgtgaacat | 180 |
| gtcggatacg | tttggtatga | acggtgtttt | gagctgcccc | aattactgcg | gcaagaaaga | 240 |
| ctcgttttgc | ggtttggctc | cgcaacgcat | gaggcctggg | tgtatcttaa | tggccactta | 300 |
| atcacgcatc | acaagggtgg | ctttacaccg | tttgaagtag | aaattaatga | cgacttagtg | 360 |
| actggtgaga | atcgactgac | ggttaaactt | agtaatatgc | ttgactatac | aactttgccg | 420 |
| gtcggacatt | acaaagaaac | gcaaaatgag | acgggccaac | gggtacggca | attagatgaa | 480 |
| aattttgact | tctttaatta | tgcggggtta | cagcgtcctg | taaaaatcta | cagtacgcca | 540 |
| cacagctata | ttcgagacat | tacgttgacg | cctaaggtta | atttgaccaa | tcactcggcg | 600 |
| gtggttaatg | gtgaaattga | cggtaggc | gatgttgaac | aggtagtcgt | cacgatctta | 660 |
| gacgaagata | accagattgt | tggtaccacg | agtgggaaaa | cactggcaat | tgagttgaac | 720 |
| tcagttcatc | tatggcagcc | gggaaaggcc | tacctgtatc | gcgctaaagt | agaattgtat | 780 |
| caggcgggc | aagtgattga | tacgtacatc | gaggcgtttg | gcattcggca | aattgcggtc | 840 |
| aaggctggta | aattttttgat | taacgggcag | cccttttact | tcaaaggatt | tgggaaacac | 900 |
| gaagacgctt | atattcatgg | tcgagggtta | agcgaaccac | agaatgtctt | ggatttgagc | 960 |
| ctaatgaagc | agatgggggc | taattcattc | cgaacgtccc | attacccgta | ttcagaagaa | 1020 |
| atgatgcggc | tatgtgatcg | tgaggggatc | gttgtgattg | atgaggtgcc | ggcagttgga | 1080 |
| ttgatgctgt | cctttacctt | tgatgtttcg | gcactagaaa | aggatgattt | tgaagacgat | 1140 |
| acgtgggaaa | aattacggac | ggctgaggcc | catcgtcagg | cgatcactga | gatgattgat | 1200 |
| cgtgataaaa | atcatgcctc | agtggtgatg | tggtcaatct | ctaatgaggc | cgccaacttt | 1260 |
| tccaagggggg | cctatgagta | ctttaagccg | ttatttgatc | tggctcgcaa | gctggatcca | 1320 |
| cagcaacgac | catgcacgta | taccagtatt | atgatgacaa | cgttaaaaac | agatcggtgt | 1380 |
| ttggcactag | ccgatgtgat | tgcgctgaac | cgatactatg | gttggtatat | gggcaatggt | 1440 |
| gatttgaaag | cagcagaaac | tgcgacgcgc | gaagaacttt | tagcttatca | ggcaaagttc | 1500 |
| ccagacaagc | caatcatgta | taccgaatat | ggtgcggata | cgattgcggg | gttgcatagt | 1560 |
| aattacgatg | agccgttttc | cgaagagttc | caagaagatt | actatcggat | gtgtagtcgg | 1620 |
| gttttttgatg | aagtgactaa | ctttgttggc | gagcaacttt | ggaattttgc | tgatttccaa | 1680 |
| acaaaatttg | ggattcaacg | cgttcaagga | aataagaagg | ggattttttac | ccgagcgcgt | 1740 |
| gaacccaaaa | tggtggttcg | gtatttaaca | caacggtggc | ggaatattcc | ggactttaat | 1800 |
| tataaaaaat | gctag | | | | | 1815 |

<210> SEQ ID NO 9
<211> LENGTH: 604
<212> TYPE: PRT
<213> ORGANISM: Lactobacillus brevis

<400> SEQUENCE: 9

-continued

```
Met Leu Tyr Pro Met Glu Thr Ala Ser Arg Val Val Leu Asp Leu Ser
1               5                   10                  15

Gly Val Trp Arg Phe Met Ile Asp Lys Glu Gln Ile Pro Val Asp Val
            20                  25                  30

Thr Arg Pro Leu Pro Ala Thr Leu Ser Met Ala Val Pro Ala Ser Phe
        35                  40                  45

Asn Asp Gln Thr Ala Ser Lys Glu Ile Arg Glu His Val Gly Tyr Val
    50                  55                  60

Trp Tyr Glu Arg Cys Phe Glu Leu Pro Gln Leu Leu Arg Gln Glu Arg
65                  70                  75                  80

Leu Val Leu Arg Phe Gly Ser Ala Thr His Glu Ala Trp Val Tyr Leu
                85                  90                  95

Asn Gly His Leu Ile Thr His His Lys Gly Gly Phe Thr Pro Phe Glu
            100                 105                 110

Val Glu Ile Asn Asp Asp Leu Val Thr Gly Glu Asn Arg Leu Thr Val
        115                 120                 125

Lys Leu Ser Asn Met Leu Asp Tyr Thr Thr Leu Pro Val Gly His Tyr
    130                 135                 140

Lys Glu Thr Gln Asn Glu Thr Gly Gln Arg Val Arg Gln Leu Asp Glu
145                 150                 155                 160

Asn Phe Asp Phe Phe Asn Tyr Ala Gly Leu Gln Arg Pro Val Lys Ile
                165                 170                 175

Tyr Ser Thr Pro His Ser Tyr Ile Arg Asp Ile Thr Leu Thr Pro Lys
            180                 185                 190

Val Asn Leu Thr Asn His Ser Ala Val Val Asn Gly Glu Ile Glu Thr
        195                 200                 205

Val Gly Asp Val Glu Gln Val Val Thr Ile Leu Asp Glu Asp Asn
    210                 215                 220

Gln Ile Val Gly Thr Thr Ser Gly Lys Thr Leu Ala Ile Glu Leu Asn
225                 230                 235                 240

Ser Val His Leu Trp Gln Pro Gly Lys Ala Tyr Leu Tyr Arg Ala Lys
                245                 250                 255

Val Glu Leu Tyr Gln Ala Gly Gln Val Ile Asp Thr Tyr Ile Glu Ala
            260                 265                 270

Phe Gly Ile Arg Gln Ile Ala Val Lys Ala Gly Lys Phe Leu Ile Asn
        275                 280                 285

Gly Gln Pro Phe Tyr Phe Lys Gly Phe Gly Lys His Glu Asp Ala Tyr
    290                 295                 300

Ile His Gly Arg Gly Leu Ser Glu Pro Gln Asn Val Leu Asp Leu Ser
305                 310                 315                 320

Leu Met Lys Gln Met Gly Ala Asn Ser Phe Arg Thr Ser His Tyr Pro
                325                 330                 335

Tyr Ser Glu Glu Met Met Arg Leu Cys Asp Arg Glu Gly Ile Val Val
            340                 345                 350

Ile Asp Glu Val Pro Ala Val Gly Leu Met Leu Ser Phe Thr Phe Asp
        355                 360                 365

Val Ser Ala Leu Glu Lys Asp Asp Phe Glu Asp Asp Thr Trp Glu Lys
    370                 375                 380

Leu Arg Thr Ala Glu Ala His Arg Gln Ala Ile Thr Glu Met Ile Asp
385                 390                 395                 400

Arg Asp Lys Asn His Ala Ser Val Val Met Trp Ser Ile Ser Asn Glu
                405                 410                 415

Ala Ala Asn Phe Ser Lys Gly Ala Tyr Glu Tyr Phe Lys Pro Leu Phe
```

```
                    420              425              430
Asp Leu Ala Arg Lys Leu Asp Pro Gln Gln Arg Pro Cys Thr Tyr Thr
                435              440              445

Ser Ile Met Met Thr Thr Leu Lys Thr Asp Arg Cys Leu Ala Leu Ala
    450              455              460

Asp Val Ile Ala Leu Asn Arg Tyr Tyr Gly Trp Tyr Met Gly Asn Gly
465              470              475              480

Asp Leu Lys Ala Ala Glu Thr Ala Thr Arg Glu Glu Leu Leu Ala Tyr
                485              490              495

Gln Ala Lys Phe Pro Asp Lys Pro Ile Met Tyr Thr Glu Tyr Gly Ala
            500              505              510

Asp Thr Ile Ala Gly Leu His Ser Asn Tyr Asp Glu Pro Phe Ser Glu
        515              520              525

Glu Phe Gln Glu Asp Tyr Tyr Arg Met Cys Ser Arg Val Phe Asp Glu
    530              535              540

Val Thr Asn Phe Val Gly Glu Gln Leu Trp Asn Phe Ala Asp Phe Gln
545              550              555              560

Thr Lys Phe Gly Ile Gln Arg Val Gln Gly Asn Lys Lys Gly Ile Phe
                565              570              575

Thr Arg Ala Arg Glu Pro Lys Met Val Val Arg Tyr Leu Thr Gln Arg
            580              585              590

Trp Arg Asn Ile Pro Asp Phe Asn Tyr Lys Lys Cys
        595              600

<210> SEQ ID NO 10
<211> LENGTH: 1815
<212> TYPE: DNA
<213> ORGANISM: Lactobacillus brevis

<400> SEQUENCE: 10
atgttatatc caatggaaac agcgtcacga gtggttttag atttatcagg tgtctggcgg      60
tttatgattg ataaagaaca gataccagtt gatgtgactc gtccgttgcc ggcaacctta     120
tcgatggcag ttccagcttc atttaacgat cagacggcat caaaagagat ccgtgaacat     180
gtcggatacg tttggtatga acggtgtttt gagctgcccc aattactgcg gcaagaaaga     240
ctcgttttgc ggtttggctc cgcaacgcat gaggcctggg tgtatcttaa tggccactta     300
atcacgcatc acaagggtgg ctttacaccg tttgaagtag aaattaatga cgacttagtg     360
actggtgaga atcgactgac ggttaaactt agtaatatgc ttgactatac aactttgccg     420
gtcggacatt acaagaaac gcaaaatgag acgggccaac gggtacggca attagatgaa     480
aattttgact tctttaatta tgcggggtta cagcgtcctg taaaaatcta cagtacgcca     540
cacagctata ttcgagacat tacgttgacg cctaaggtta atttgaccaa tcactcggcg     600
gtggttaatg gtgaaattga cggtaggc gatgttgaac aggtagtcgt cacgatctta     660
gacgaagata accagattgt tggtaccacg agtgggaaaa cactggcaat tgagttgaac     720
tcagttcatc tatggcagcc gggaaaggcc tacctgtatc gcgctaaagt agaattgtat     780
caggcggggc aagtgattga tacgtacatc gaggcgtttg gcattcggca aattgcggtc     840
aaggctggta aattttgat taacgggcag cccttttact tcaaaggatt tgggaaacac     900
gaagacgctt atattcatgg tcgagggtta agcgaaccac agaatgtctt ggatttgagc     960
ctaatgaagc agatggggc taattcattc cgaacgtccc attacccgta ttcagaagaa    1020
atgatgcggc tatgtgatcg tgaggggatc gttgtgattg atgaggtgcc ggcagttgga    1080
```

-continued

```
ttgatgctgt cctttacctt tgatgtttcg gcactagaaa aggatgattt tgaagacgat    1140
acgtgggaaa aattacggac ggctgaggcc catcgtcagg cgatcactga gatgattgat    1200
cgtgataaaa atcatgcctc agtggtgatg tggtcaatct ctaatgaggc cgccaacttt    1260 tccaagggg cctatgagta ctttaagccg ttatttgatc tggctcgcaa gctggatcca    1320
cagcaacgac catgcacgta taccagtatt atgatgacaa cgttaaaaac agatcggtgt    1380
ttggcactag ccgatgtgat tgcgctgaac cgatactatg gttggtatat ggcaatggt    1440 gatttgaaag cagcagaaac tgcgacgcgc gaagaacttt tagcttatca ggcaaagttc    1500
ccagacaagc caatcatgta taccgaatat ggtgcggata cgattgcggg gttgcatagt    1560
aattacgatg agccgttttc cgaagagttc caagaagatt actatcggat gtgtagtcgg    1620 gttttgatg aagtgactaa ctttgttggc gagcaacttt ggaattttgc tgatttccaa    1680
acaaaattta gcattcaacg cgttcaagga aataagaagg ggattttac ccgagcgcgt    1740 gaacccaaaa tggtggttcg gtatttaaca caacggtggc ggaatattcc ggactttaat    1800
tataaaaaat gctag                                                    1815
```

<210> SEQ ID NO 11
<211> LENGTH: 604
<212> TYPE: PRT
<213> ORGANISM: Lactobacillus brevis

<400> SEQUENCE: 11

```
Met Leu Tyr Pro Met Glu Thr Ala Ser Arg Val Val Leu Asp Leu Ser
1               5                   10                  15

Gly Val Trp Arg Phe Met Ile Asp Lys Glu Gln Ile Pro Val Asp Val
            20                  25                  30

Thr Arg Pro Leu Pro Ala Thr Leu Ser Met Ala Val Pro Ala Ser Phe
        35                  40                  45

Asn Asp Gln Thr Ala Ser Lys Glu Ile Arg Glu His Val Gly Tyr Val
    50                  55                  60

Trp Tyr Glu Arg Cys Phe Glu Leu Pro Gln Leu Leu Arg Gln Glu Arg
65                  70                  75                  80

Leu Val Leu Arg Phe Gly Ser Ala Thr His Glu Ala Trp Val Tyr Leu
                85                  90                  95

Asn Gly His Leu Ile Thr His His Lys Gly Gly Phe Thr Pro Phe Glu
            100                 105                 110

Val Glu Ile Asn Asp Asp Leu Val Thr Gly Glu Asn Arg Leu Thr Val
        115                 120                 125

Lys Leu Ser Asn Met Leu Asp Tyr Thr Thr Leu Pro Val Gly His Tyr
    130                 135                 140

Lys Glu Thr Gln Asn Glu Thr Gly Gln Arg Val Arg Gln Leu Asp Glu
145                 150                 155                 160

Asn Phe Asp Phe Phe Asn Tyr Ala Gly Leu Gln Arg Pro Val Lys Ile
                165                 170                 175

Tyr Ser Thr Pro His Ser Tyr Ile Arg Asp Ile Thr Leu Thr Pro Lys
            180                 185                 190

Val Asn Leu Thr Asn His Ser Ala Val Val Asn Gly Glu Ile Glu Thr
        195                 200                 205

Val Gly Asp Val Glu Gln Val Val Thr Ile Leu Asp Glu Asp Asn
    210                 215                 220

Gln Ile Val Gly Thr Thr Ser Gly Lys Thr Leu Ala Ile Glu Leu Asn
225                 230                 235                 240
```

```
Ser Val His Leu Trp Gln Pro Gly Lys Ala Tyr Leu Tyr Arg Ala Lys
            245                 250                 255

Val Glu Leu Tyr Gln Ala Gly Gln Val Ile Asp Thr Tyr Ile Glu Ala
        260                 265                 270

Phe Gly Ile Arg Gln Ile Ala Val Lys Ala Gly Lys Phe Leu Ile Asn
            275                 280                 285

Gly Gln Pro Phe Tyr Phe Lys Gly Phe Gly Lys His Glu Asp Ala Tyr
        290                 295                 300

Ile His Gly Arg Gly Leu Ser Glu Pro Gln Asn Val Leu Asp Leu Ser
305                 310                 315                 320

Leu Met Lys Gln Met Gly Ala Asn Ser Phe Arg Thr Ser His Tyr Pro
                325                 330                 335

Tyr Ser Glu Glu Met Met Arg Leu Cys Asp Arg Glu Gly Ile Val Val
            340                 345                 350

Ile Asp Glu Val Pro Ala Val Gly Leu Met Leu Ser Phe Thr Phe Asp
        355                 360                 365

Val Ser Ala Leu Glu Lys Asp Asp Phe Glu Asp Thr Trp Glu Lys
        370                 375                 380

Leu Arg Thr Ala Glu Ala His Arg Gln Ala Ile Thr Glu Met Ile Asp
385                 390                 395                 400

Arg Asp Lys Asn His Ala Ser Val Val Met Trp Ser Ile Ser Asn Glu
                405                 410                 415

Ala Ala Asn Phe Ser Lys Gly Ala Tyr Glu Tyr Phe Lys Pro Leu Phe
            420                 425                 430

Asp Leu Ala Arg Lys Leu Asp Pro Gln Gln Arg Pro Cys Thr Tyr Thr
        435                 440                 445

Ser Ile Met Met Thr Thr Leu Lys Thr Asp Arg Cys Leu Ala Leu Ala
450                 455                 460

Asp Val Ile Ala Leu Asn Arg Tyr Tyr Gly Trp Tyr Met Gly Asn Gly
465                 470                 475                 480

Asp Leu Lys Ala Ala Glu Thr Ala Thr Arg Glu Glu Leu Leu Ala Tyr
                485                 490                 495

Gln Ala Lys Phe Pro Asp Lys Pro Ile Met Tyr Thr Glu Tyr Gly Ala
            500                 505                 510

Asp Thr Ile Ala Gly Leu His Ser Asn Tyr Asp Glu Pro Phe Ser Glu
        515                 520                 525

Glu Phe Gln Glu Asp Tyr Tyr Arg Met Cys Ser Arg Val Phe Asp Glu
        530                 535                 540

Val Thr Asn Phe Val Gly Glu Gln Leu Trp Asn Phe Ala Asp Phe Gln
545                 550                 555                 560

Thr Lys Phe Ser Ile Gln Arg Val Gln Gly Asn Lys Lys Gly Ile Phe
                565                 570                 575

Thr Arg Ala Arg Glu Pro Lys Met Val Val Arg Tyr Leu Thr Gln Arg
            580                 585                 590

Trp Arg Asn Ile Pro Asp Phe Asn Tyr Lys Lys Cys
            595                 600

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
agcattcaac gcgttcaagg aaataa                                          26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 aaatttgtt tggaaatcag caaaat                                           26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgctagaagc ttgcggccgc actcgag                                         27

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15 tttttttataa ttaaagtccg gaatattc                                       28

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: Any amino acid
<220> FEATURE:
<221> NAME/KEY: MISC_FEATURE
<222> LOCATION: (1)..(8)
<223> OTHER INFORMATION: This region may encompass 0-8 residues, wherein
      some positions may be absent
<220> FEATURE:
<221> NAME/KEY: MOD_RES
<222> LOCATION: (10)..(11)
<223> OTHER INFORMATION: Any amino acid
<220> FEATURE:
<221> NAME/KEY: MISC_FEATURE
<222> LOCATION: (10)..(11)
<223> OTHER INFORMATION: This region may encompass 0-2 residues, wherein
      some positions may be absent

<400> SEQUENCE: 16

Xaa Xaa Xaa Xaa Xaa Xaa Xaa Xaa Cys Xaa Xaa
1               5                   10

<210> SEQ ID NO 17
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 17

Gly Leu Cys Gly Arg
1               5
```

MUTANT LACTOBACILLUS BETA-GLUCURONIDASE ENZYMES WITH ENHANCED ENZYMATIC ACTIVITY

SEQUENCE LISTING

The instant application contains a Sequence Listing which has been submitted electronically in ASCII format and is hereby incorporated by reference in its entirety. Said ASCII copy, created on May 4, 2016, is named IMJ_004_Sequence_Listing.txt and is 38,465 bytes in size.

BACKGROUND OF THE INVENTION

In mammals, glucuronidation is one of the principle means of detoxifying or inactivating compounds using the UDP glucuronyl transferase system. Compounds are conjugated by the glucoronyl transferase system to form glucuronides, which are then secreted in urine or into the lower intestine in bile. Furthermore, microorganisms in the gut, such as *Escherichia coli*, have evolved to utilize the excreted β-glucuronides as a carbon source. The β-glucuronidase (BGUS) enzyme catalyzes the hydrolysis of a wide variety of β-glucuronides. Thus, BGUS enzyme activity been reported in those organisms that utilize glucuronidation as a detoxification pathway, as well as in some of their endogenous microbe populations. All vertebrates and many mollusks, as well as certain bacteria, exhibit BGUS enzyme activity, whereas insects and plants that utilize a different detoxification pathway typically do not exhibit BGUS enzyme activity.

Given the key role of glucuronidation in detoxification of compounds, the BGUS enzyme has been used for detection of drugs in bodily samples, such as to detect the presence of illicit drugs in bodily samples of criminal suspects. For example, a bodily sample can be tested for the presence of a suspected drug by detecting the hydrolysis of the glucuronide form of the drug by BGUS.

Commercially available preparations of BGUS enzyme, for use for example in drug testing, include crude extract forms of the *E. coli*, snail and abalone versions of the enzyme. While these preparations are effective in hydrolyzing glucuronides, they typically include other proteins in addition to the BGUS, which may interfere with enzyme activity. Moreover, importantly, their level of enzyme activity is such that they typically require at least several hours (e.g., three hours or more) to analyze a sample. Including sample preparation time and analysis time, this means that evaluation of a drug sample typically can take at least two days using currently commercially available BGUS preparations. Furthermore, currently commercially available BGUS preparations are more efficient at neutral pH but are less efficient at lower pH (e.g., below 6.8).

Accordingly, there is a need for BGUS enzymes with enhanced activity that are more efficient for use in drug testing.

SUMMARY OF THE INVENTION

The invention provides mutant forms of *Lactobacillus brevis* strain 269Y BGUS enzymes that exhibit enhanced enzymatic activity at low pH (i.e., below pH 6.8, such as at pH 5.2 or pH 4.5) as compared to wild type enzyme. Moreover, the mutant forms of BGUS described herein exhibit higher thermal stability (e.g., at 55° C. or 65° C.) than the wild type enzyme. The enzymes of the invention advantageously allow for accurate analysis of bodily samples for the presence of drugs in 30 minutes or less, as compared to the several hours needed using the current commercially available enzyme preparations, thereby allowing for completion of analyses within a shorter time frame than previously possible. Moreover, an advantageous feature of the enhanced activity of the mutant BGUS enzymes at low pH, as described herein, is that this allows for greater compatibility with arylsulfatases and down-stream analytics that use low pH conditions (e.g., volatile buffers used in downstream mass spectrometry analysis). Furthermore, the mutant enzymes of the invention are produced recombinantly and thus can be prepared in a highly purified form without contaminating non-BGUS proteins and with a higher temperature stability.

In one aspect, the invention pertains to a mutated *Lactobacillus brevis* strain 269Y β-glucuronidase (LbGUS) enzyme comprising a substitution of an amino acid corresponding to G564 in SEQ ID NO: 2 with an amino acid comprising a side chain comprising a non-aromatic hydroxyl group or histidine or asparagine. In one embodiment of the mutated LbGUS enzyme, the amino acid corresponding to G564 in SEQ ID NO: 2 is substituted with a serine or threonine. In another embodiment, the amino acid corresponding to G564 in SEQ ID NO: 2 is substituted with a serine. In one embodiment, the mutated LbGUS enzyme has the amino acid sequence shown in SEQ ID NO: 7. In one embodiment, the mutated LbGUS enzyme is encoded by the nucleotide sequence shown in SEQ ID NO: 6.

In another aspect, the invention pertains to a mutated *Lactobacillus brevis* strain 269Y β-glucuronidase (LbGUS) enzyme comprising an addition of a cysteine residue appended at or near the carboxy terminus of the enzyme, wherein the carboxy terminus has the sequence: $Xaa_{0-8}$-Cys-$Xaa_{0-2}$, wherein Xaa=any amino acid (SEQ ID NO: 16). In one embodiment, the mutated LbGUS enzyme having a cysteine appended at or near the carboxy terminus has the amino acid sequence shown in SEQ ID NO: 9. In one embodiment, the mutated LbGUS enzyme is encoded by the nucleotide sequence shown in SEQ ID NO: 8.

In yet another aspect, the invention pertains to a mutated *Lactobacillus brevis* strain 269Y β-glucuronidase (LbGUS) enzyme comprising:

(i) a substitution of an amino acid corresponding to G564 in SEQ ID NO: 2 with an amino acid comprising a side chain comprising a non-aromatic hydroxyl group or histidine or asparagine; and (ii) an addition of a cysteine residue appended at or near the carboxy terminus of the enzyme, wherein the carboxy terminus has the sequence: $Xaa_{0-8}$-Cys-$Xaa_{0-2}$, wherein Xaa=any amino acid (SEQ ID NO: 16).

In one embodiment of the mutated LbGUS enzyme, the amino acid corresponding to G564 in SEQ ID NO: 2 is substituted with a serine or threonine. In another embodiment, the amino acid corresponding to G564 in SEQ ID NO: 2 is substituted with a serine. In one embodiment, the mutated LbGUS enzyme has the amino acid sequence shown in SEQ ID NO: 11. In one embodiment, the mutated LbGUS enzyme is encoded by the nucleotide sequence shown in SEQ ID NO: 10.

In another aspect, the invention provides a packaged formulation comprising a container comprising a preparation of any of the mutated LbGUS enzymes disclosed herein, wherein the preparation has an enzymatic activity of at least 5,000 Units/ml or 5,000 Units/mg. In one embodiment, the preparation is an aqueous solution with an enzymatic activity of at least 50,000 Units/ml. In another embodiment, the preparation is a lyophilized preparation with an enzymatic activity of at least 50,000 Units/mg. In one embodiment, the preparation is stable at least six months at 2-8° C. In one embodiment, the preparation lacks detectable sulfatase activity.

In yet another aspect, the invention provides a method of hydrolyzing a substrate comprising a glucuronide linkage, the method comprising contacting the substrate with any of the mutated LbGUS enzymes disclosed herein under conditions such that hydrolysis of the glucuronide linkage occurs. In one embodiment, the substrate is an opiate glucuronide. In various embodiments, the opiate glucuronide is selected from the group consisting of morphine-3β-D-glucuronide, morphine-6β-D-glucuronide, codeine-6β-D-glucuronide, hydromorphone-3β-D-glucuronide, oxymorphone-3β-D-glucuronide, and combinations thereof. In another embodiment, the substrate is a benzodiazepine glucuronide. In various embodiments, the benzodiazepine glucuronide is selected from the group consisting of oxazepam-glucuronide, lorazepam-glucuronide, temazepam-glucuronide, alprazolam, alpha-hydroxy-alprazolam glucuronide, nordiazepam, 7-amino-clonozepam, and combinations thereof. In various embodiments, the substrate is in a sample of blood, urine, tissue or meconium obtained from a subject.

Other features and aspects of the invention are described in further detail herein.

BRIEF DESCRIPTION OF THE DRAWINGS

FIG. 1 is an alignment of the amino acid sequence of the *L. brevis* strain 269Y wild type BGUS enzyme (SEQ ID NO: 2) as compared to the *L. brevis* strain RO1 wild type BGUS enzyme (SEQ ID NO: 5). The four amino acid differences between the two sequences (at amino acid positions 226, 272, 447 and 568) are highlighted in bold and underlined.

FIG. 2 is an alignment of the amino acid sequences of the *L. brevis* strain 269Y BGUS enzyme mutants Lb1F (SEQ ID NO: 7), Lb-1C (SEQ ID NO: 9) and Lb1F-1C (SEQ ID NO: 11), as compared to the wild type sequence (LbGUS (SEQ ID NO: 2)). The G564S mutation in the Lb1F and Lb1F-1C mutants, and the C-terminal cysteine addition in the Lb-1C and Lb1F-1C mutants, are highlighted in bold and underlined.

DETAILED DESCRIPTION OF THE INVENTION

Figure 3:
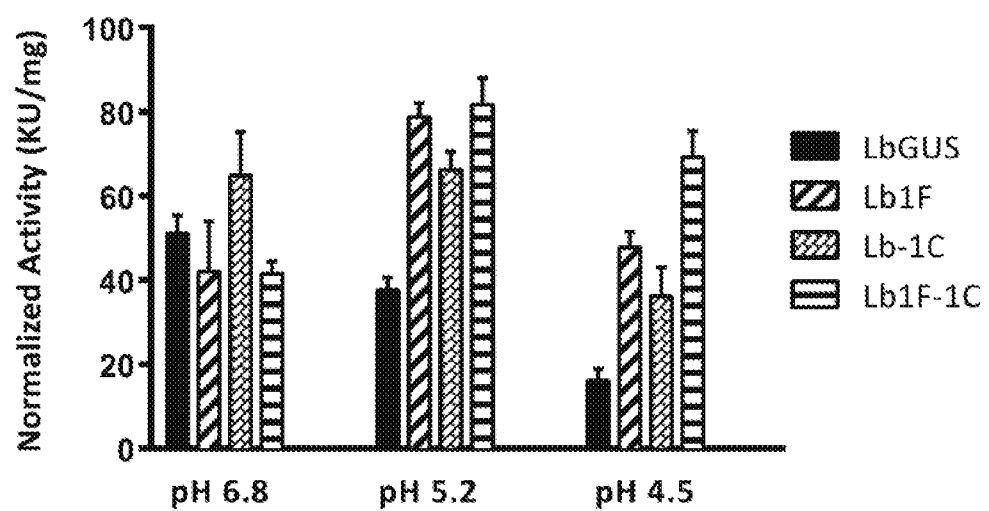
FIG. 3 is a bar graph showing the enzymatic activity at pH 6.8, pH 5.2 and pH 4.5 of the Lb1F, Lb-1C and Lb1F-1C mutant enzymes as compared to the wild type enzyme (LbGUS). The results show normalized activity (KU/mg).

The invention pertains to mutated *Lactobacillus brevis* stain 269Y β-glucuronidase enzymes having enhanced enzymatic activity at low pH (e.g., below pH 6.8) and increased thermostability at high temperatures (e.g., at 55° C. or 65° C.) as compared to the wild type enzyme, as well as packaged formulations thereof and methods of using the enzymes for hydrolysis of glucuronide linkages. As used herein, enhanced enzymatic activity at "low pH" is intended to refer to enhanced BGUS activity at a pH below neutral pH, such as below pH 6.8, or below pH 6.0, or below pH 5.5, or below pH 5.2 or below pH 5.0, or between pH 4.5-5.2, or at pH 5.2 or at pH 4.5.

Various aspects of the invention are described in further detail in the following subsections.

I. Mutated *L. brevis* Strain 269Y β-Glucuronidase Enzymes

A. Position 564 Substitutions

As used herein, the term "β-glucuronidase enzyme", also referred to as "β-glucuronidase" or "BGUS", refers to an enzyme that hydrolyzes β-glucuronide linkages. A "wild type" BGUS enzyme refers to the naturally occurring form of the enzyme. A "mutated" BGUS enzyme refers to a modified form of the enzyme in which one or more modifications, such as amino acid substitutions, deletions and/or insertions, have been made such that the amino acid sequence of the mutated BGUS enzyme differs from the wild type amino acid sequence. The nucleotide sequence encoding wild type *L. brevis* 269Y strain BGUS is shown in SEQ ID NO: 1. The amino acid sequence of wild type *L. brevis* 269Y strain BGUS is shown in SEQ ID NO: 2. Cloning of the wild type *L. brevis* 269Y strain BGUS is described in detail in Example 1. Comparison of the amino acid sequence of the wild-type *L. brevis* 269Y strain BGUS amino acid sequence to the *L. brevis* RO1 strain BGUS amino acid sequence (the cloning of which is described in Kim, H. S. et al. (2009) *J. Microbiol. Biotechnol.* 19:1650-1655) is shown in FIG. 1, with the four amino acid differences between the BGUS sequence of the two strains (at amino acid positions 226, 272, 447 and 568) highlighted in bold and underlined.

It has now been discovered that a single amino acid substitution of an amino acid corresponding to G564 in SEQ ID NO: 2 (wild type *L. brevis* strain 269Y BGUS) with an amino acid comprising a side chain comprising a non-aromatic hydroxyl group, or with histidine or asparagine, creates a mutated BGUS enzyme that has significantly enhanced enzymatic activity as compared to the wild type enzyme at low pH (i.e., pH below 6.8), as well as enhanced thermostability. As used herein, a "side chain" of an amino acid refers to the "R" group in the standard generic formula for amino acids: H₂NCHRCOOH. A "non-aromatic hydroxyl group" refers to a side chain structure that contains an —OH group, but that lacks a ring structure. In one embodiment, the amino acid comprising a side chain comprising a non-aromatic hydroxyl group is serine (i.e., the mutation in the enzyme consists of a G564S substitution). In another embodiment, the amino acid comprising a side chain comprising a non-aromatic hydroxyl group is threonine (i.e., the mutation in the enzyme consists of a G564T substitution). In yet other embodiments, the amino acid comprising a side chain comprising a non-aromatic hydroxyl group can be a non-naturally occurring amino acid. Non-limiting examples of non-natural amino acids comprising a side chain comprising a non-aromatic hydroxyl group include L-iso-serine (Sigma Aldrich Product #06054), L-allo-threonine (Sigma Aldrich Product #210269), homoserine (Swiss Side Chain ID# HSER), 3-3-dihydoxyalanine (Swiss Side Chain ID# DDZ) and 2-amino-5-hydroxypentanoic acid (Swiss Side Chain ID# AA4).

The preparation of a mutant *L. brevis* strain 269Y BGUS enzyme having a single G564S substitution (referred to herein as Lb1F) is described in detail in Example 2. The full-length nucleotide sequence acid encoding the Lb1F mutant is shown in SEQ ID: 6. The full-length amino acid sequence of the Lb1F mutant is shown in SEQ ID NO: 7. The alignments of the Lb1F mutant amino acid sequences as compared to wild-type *L. brevis* strain 269Y sequence (SEQ ID NO: 2) is shown in FIG. 2.

The enzymatic activity of the Lb1F enzyme as compared to wild type is described in detail in Example 4 and shown in FIG. 3 and Table 1. This data demonstrates that the single G564S mutation imparts approximately a 2-fold enhancement in enzymatic activity of the mutant as compared to the wild-type enzyme at pH 5.2 and approximately a 3-fold enhancement in enzymatic activity of the mutant as compared to the wild type enzyme at pH 4.5. The thermostability of the Lb1F enzyme as compared to wild type is described in Example 5 and shown in Table 2. This data demonstrate that the single G564S mutation imparts significantly enhanced thermostability to the mutant enzyme at both 55° C. and 65° C.

Xiong, A-S. et al. (2007) *Prot. Eng. Design Select.* 20:319-325 has reported the preparation of a mutated *E. coli* BGUS enzyme containing six amino acid substitutions: Q493R, T509A, M532T, N550S, G559S and N566S. This mutant enzyme is reported to have improved thermostability as compared to the wild type enzyme. However, the significantly improved enzymatic activity at low pH of the single amino acid substitution, G564S, as reported herein (corresponding to position G559 of the *E. coli* BGUS enzyme), as well as the enhanced thermostability of the single amino acid substitution, G564S, as reported herein, is not disclosed in or suggested by Xiong et al.

Experiments described in U.S. Ser. No. 14/867,710 (filed Sep. 28, 2015, claiming priority to U.S. Provisional Application No. 62/056,800, filed Sep. 29, 2015), the entire contents of which is expressly incorporated herein by reference, using *E. coli* BGUS demonstrate that substitution of the wild-type G559 position, corresponding to position G564 of the *L. brevis* strain 269Y BGUS enzyme described herein, with either serine (S), threonine (T), histidine (H) or asparagine (N) leads to enhanced enzymatic activity. Accordingly, given the experimental results reported herein for the G564S substitution in the *L. brevis* strain 269Y BGUS enzyme showing enhanced enzymatic activity at low pH, as well as enhanced thermostability, for the G564S substitution, it is predicted that similar enhanced enzymatic activity at low pH and enhanced thermostability is expected for G564T, G564H and G564N substitutions as well, which mutations are also encompassed by the invention.

B. Carboxy Terminal Cysteine Residue

It has now been discovered that appending a cysteine residue at or near the carboxy terminal end of the *L. brevis* strain 269Y BGUS enzyme enhances the enzymatic activity at low pH (e.g., below pH 6.8). Accordingly, in another aspect, the invention provides a mutant *L. brevis* strain 269Y BGUS enzyme comprising an addition of a cysteine residue appended at or near the carboxy terminus of the enzyme. As used herein, "the carboxy terminus" (used interchangeably with "C-terminus", "carboxy terminal end" or "C-terminal end") of the BGUS enzyme refers to the end of the protein that terminates in a carboxyl group, according to the standard nomenclature for proteins well established in the art. As used herein, "near the C-terminal end" refers to within a few (i.e., 2-4) amino acids of the C-terminal end.

The preparation of a mutant *L. brevis* strain 269Y BGUS enzyme having a cysteine appended at the C-terminus, referred to herein as the Lb-1C mutant, is described in detail in Example 2. The full-length nucleotide sequence encoding the Lb-1C mutant is shown in SEQ ID NO: 8. The full-length amino acid sequence of the Lb-1C mutant is shown in SEQ ID NO: 9. The alignment of the Lb-1C mutant amino acid sequence as compared the to wild-type sequence (SEQ ID NO: 2) is shown in FIG. 2.

The enzymatic activity of the Lb-1C enzyme as compared to wild type is described in detail in Example 4 and shown in FIG. 3 and Table 1. This data demonstrates that the C-terminal cysteine addition imparts approximately a 2-fold enhancement in enzymatic activity of the mutant as compared to the wild-type enzyme at pH 5.2 or pH 4.5.

In one embodiment, the cysteine residue appended at or near the C-terminal end is a single cysteine residue appended at the C-terminal end (i.e., the cysteine is the last amino acid residue in the protein sequence), as in the Lb-1C mutant. In other embodiments, the cysteine appended to the C-terminus can be contained within a larger peptide. In one embodiment, the cysteine appended to the C-terminus is contained within the following sequence: $Xaa_{0-8}$-Cys-$Xaa_{0-2}$, wherein Xaa=any amino acid (SEQ ID NO: 16). For example, in one embodiment, the cysteine appended to the C-terminal end is part of a tripeptide. A preferred tripeptide for addition onto the C-terminal end has the sequence Gly-Leu-Cys (GLC). Similar tripeptides with conservative substitutions as compared to the GLC tripeptide also can be used. Alternatively, the cysteine appended to the C-terminal end can be part of, for example, a pentapeptide. A preferred pentapeptide for addition to the C-terminal end has the sequence Gly-Leu-Cys-Gly-Arg (GLCGR) (SEQ ID NO: 17).

C. Combination Mutants

In another aspect, the invention pertains to mutant *L. brevis* strain 269Y BGUS enzymes that contain two or more of the above described modifications, referred to herein as combination mutants.

Accordingly, in one embodiment, the invention provides a mutated *L. brevis* strain 269Y β-glucuronidase enzyme comprising:

(i) a substitution of an amino acid corresponding to G564 in SEQ ID NO: 2 with an amino acid comprising a side chain comprising a non-aromatic hydroxyl group or histidine or asparagine; and (ii) an addition of a cysteine residue appended at or near the carboxy terminus of the enzyme (e.g., wherein the carboxy terminus has the sequence: $Xaa_{0-8}$-Cys-$Xaa_{0-2}$, wherein Xaa=any amino acid (SEQ ID NO: 16)).

In these combination mutants having a G564 substitution, in one embodiment, the amino acid corresponding to G564 in SEQ ID NO: 2 is substituted with serine. In another embodiment, the amino acid corresponding to G564 in SEQ ID NO: 2 is substituted with threonine. In yet other embodiments, the amino acid corresponding to G564 in SEQ ID NO: 2 is substituted with a non-natural amino acid as described above in subsection IA. In yet other embodiments, the amino acid corresponding to G564 is substituted with histidine or asparagine.

The preparation of a combination mutant *L. brevis* strain 269Y BGUS enzyme having a G564S substitution and having a cysteine appended at the C-terminus, referred to herein as the Lb1F-1C mutant, is described in detail in Example 2. The full-length nucleotide sequence encoding the Lb1F-1C mutant is shown in SEQ ID NO: 10. The full-length amino acid sequence of the Lb1F-1C mutant is shown in SEQ ID NO: 11. The alignment of the Lb1F-1C mutant amino acid sequence as compared the to wild-type sequence (SEQ ID NO: 2) is shown in FIG. 2.

The enzymatic activity of the Lb1F-1C enzyme as compared to wild type is described in detail in Example 4 and shown in FIG. 3 and Table 1. This data demonstrates that the combination of the G564S substitution and the C-terminal cysteine addition imparts over a 2-fold enhancement in enzymatic activity of the mutant as compared to the wild-type enzyme at pH 5.2 and over a 4-fold enhancement in the enzymatic activity of the mutant at pH 4.5.

In one embodiment, the cysteine residue appended at or near the C-terminal end is a single cysteine residue appended at the C-terminal end (i.e., the cysteine is the last amino acid residue in the protein sequence), as in the Lb1F-1C mutant. In other combination mutants having a cysteine residue appended at or near the carboxy terminus, a tripeptide Glycine-Leucine-Cysteine (GLC) or a pentapeptide Gly-Leu-Cys-Gly-Arg (GLCGR (SEQ ID NO: 17)) can be appended at the carboxy terminus.

In another embodiment, a combination mutant that comprises a substitution at position 564 and that has a cysteine residue appended at or near the C-terminal end has position 564 substituted with Ser (S), Thr (T), His (H) or Asn (N) and wherein the C-terminal end has the following sequence: $Xaa_{0.8}$-Cys-$Xaa_{0.2}$, wherein Xaa=any amino acid (SEQ ID NO: 16).

II. Preparation of Mutant Enzymes

The BGUS enzymes of the invention can be prepared using standard recombinant DNA techniques. A preferred method for mutation is to perform overlap extension PCR using primers that incorporate the desired mutation(s), as described in detail in Example 2. Other methods known in the art for protein mutagenesis, however, are also suitable. Once a nucleic acid fragment encoding the desired mutant BGUS enzyme has been obtained, the fragment can be inserted into a suitable expression vector, transformed into a suitable host cell and the mutant protein expressed recombinantly by culturing of the host cell. Representative non-limiting examples of suitable expression vectors and host cells are described in Example 2, although the skilled artisan will appreciate that any of a variety of expression systems known in the art can be used.

Following recombinant expression of the mutant BGUS enzyme, the protein can be purified using standard protein purification techniques. For example, standard affinity chromatography methods, such as immunoaffinity chromatography using an anti-BGUS antibody or metal ion affinity chromatography using nickel, cobalt or copper resin, can be used.

III. Packaged Formulations

In another aspect, the invention pertains to packaged formulations that comprise a mutant BGUS enzyme of the invention. These packaged formulations comprise a container comprising a preparation of the mutant BGUS enzyme. Non-limiting examples of suitable containers include, bottles, tubes, vials, ampules and the like. Preferably, the container is glass or plastic, although other suitable materials are known in the art. The preparation of the mutant BGUS enzyme can be in liquid or solid form. Thus, in one embodiment, the enzyme preparation is an aqueous solution. In another embodiment, the enzyme preparation is a lyophilized preparation. Lyophilized preparations can be packaged with instructions for reconstituting the enzyme into a liquid solution (e.g., an aqueous solution).

Preferably, the preparation of β-glucuronidase enzyme in the packaged formulation has an enzymatic activity of at least 5,000 Units/ml or 5,000 Units/mg, more preferably at least 10,000 Units/ml or 10,000 Units/mg, even more preferably at least 25,000 Units/ml or 25,000 Units/mg and even more preferably 50,000 Units/ml or 50,000 Units/mg. In one embodiment, the β-glucuronidase enzyme in the preparation is in an aqueous solution with an enzymatic activity of at least 5,000 Units/ml, or at least 10,000 Units/ml or at least 25,000 Units/ml or at least 50,000 Units/ml. In another embodiment, the β-glucuronidase enzyme in the preparation is in lyophilized form with an enzymatic activity of at least 5,000 Units/mg, or at least 10,000 Units/mg or at least 25,000 Units/mg or at least 50,000 Units/mg. In yet another embodiment, the β-glucuronidase enzyme in the preparation is in lyophilized form that when reconstituted as an aqueous solution has an enzymatic activity of at least 5,000 Units/ml, or at least 10,000 Units/ml or at least 25,000 Units/ml or at least 50,000 Units/ml.

The specific activity of the enzyme in the preparation, in Units/ml or Units/mg, can be determined using a standardized glucuronide linkage hydrolysis assay using phenolphthalein-glucuronide as the substrate. The standardization of the specific activity of BGUS has been well established in the art. Thus, 1 Unit of BGUS activity is defined as an amount of enzyme that liberates 1 μg of phenolphthalein from phenolphthalein-glucuronide in 1 hour. An exemplary standardized assay that can be used to determine the specific activity (in Units/ml or Units/mg) of an enzyme preparation (e.g., an aqueous solution or lyophilized preparation) is described in further detail in Example 3. The skilled artisan will appreciate that other protocols for the enzyme assay are also suitable (e.g., such as those described by Sigma Aldrich Chemical Co.). The calculation of Units/ml or Units/mg based on the results of the enzymatic assay also is described in detail in Example 3.

In a preferred embodiment, the preparation containing the mutant BGUS enzyme is substantially free of other non-BGUS proteins. As used herein, "substantially free" refers to less than 5%, preferably less than 3%, even more preferably less than 1% of contamination non-BGUS proteins. In another preferred embodiment, the preparation containing the mutant BGUS enzyme lacks detectable sulfatase activity. In yet another preferred embodiment, the preparation containing the mutant BGUS enzyme is stable at least one month, more preferably at least three months, and even more preferably at least six months at 2-8° C. As used herein, "stable" refers to the mutant BGUS enzyme in the preparation maintaining at least 90%, more preferably at least 95%, even more preferably at least 98% of its enzymatic activity over the indicated time at the indicated temperature.

IV. Methods of Use

The mutant BGUS enzymes of the invention exhibit enhanced ability to hydrolyze glucuronide linkages at low pH (i.e., below pH 6.8) as compared to the wild type enzyme. Accordingly, the mutant enzymes can be used in methods for hydrolysis of glucuronide substrates. These methods are particularly useful for analyzing bodily samples for the presence of drugs through detection of the glucuronide detoxification products of the drugs. Thus, in another aspect the invention pertains to a method of hydrolyzing a substrate comprising a glucuronide linkage, the method comprising contacting the substrate with a mutant β-glucuronidase enzyme of the invention under conditions such that hydrolysis of the glucuronide linkage occurs. Any of the mutant enzymes of the invention, including those having a single modification and those having more than one modification (i.e., combination mutants) can be used in the method.

In one embodiment, the substrate is an opiate glucuronide. Non-limiting examples of suitable opiate glucuronide substrates include morphine-3β-D-glucuronide, morphine-6β-D-glucuronide, codeine-6β-D-glucuronide, hydromorphone-3β-D-glucuronide, oxymorphone-3β-D-glucuronide, and combinations thereof. In another embodiment, the substrate is a benzodiazepine glucuronide. Non-limiting examples of suitable benzodiazepine glucuronide substrates include the glucuronides of oxazepam, lorazepam, temazepam, and alpha-hydroxy-alprazolam. Other suitable substrates include the glucuronides of buprenorphine, norbuprenorphine, 11-nor-Δ9-tetrahydrocannabinol-9-carboxylic acid, testosterone, androsterone, tapentadol, cyclobenzaprine, amitripyline and combinations thereof.

The methods of the invention can be used on a variety of different bodily samples. Non-limiting examples of suitable bodily samples include blood, urine, tissue or meconium obtained from a subject. Such samples can be obtained, stored and prepared for analysis using standard methods well established in the art.

Following hydrolysis by the enzyme, the cleavage products in the sample can be analyzed by standard methodologies, such as high performance liquid chromatography (HPLC), gas chromatography (GC) and/or mass spectrometry (MS). Such approaches for analysis of bodily samples for the presence of drugs are well established in the art. For example, a completely automated workflow for the hydrolysis and analysis of urine samples by LC-MS/MS, which can be applied using the mutant enzymes of the invention for hydrolysis, is described in Cabrices, O. G. et al., GERSTEL AppNote AN/2014/4-7.

In addition to its use in drug testing, a mutated BGUS enzyme of the invention can be used in essentially any other methodology for which the wild type BGUS enzyme can be used. For example, U.S. Pat. No. 5,599,670 describes a gene fusion system in which DNA encoding a BGUS enzyme is fused to DNA encoding a gene of interest to create a reporter gene system that can be used for a wide variety of genetic engineering purposes. Accordingly, the mutated BGUS enzymes of the invention can be used in this gene fusion system to enhance the enzymatic activity of the BGUS portion of the fusion protein.

The present invention is further illustrated by the following examples, which should not be construed as further limiting. The contents of Sequence Listing, figures and all references, patents and published patent applications cited throughout this application are expressly incorporated herein by reference.

EXAMPLES

Example 1: Cloning of *L. brevis* Strain 269Y β-Glucuronidase (BGUS) Gene

In this example, the wild type *Lactobacillus brevis* strain 269Y BGUS sequence was cloned by polymerase chain reaction (PCR). The forward primer used for PCR had the following sequence: gagagacatatgttatatccaatggaaacag (SEQ ID NO: 3). The reverse primer for PCR had the following sequence: gagagaaagcttctatttttataattaaagtccggaatattc (SEQ ID NO: 4). The forward primer contains an NdeI restriction site and the reverse primer contains a HindIII restriction site (underlined in the primer sequences shown above).

The *L. brevis* strain 269Y is publicly available (ATCC 8287D). To isolate a sample of *L. brevis* strain 269Y genomic DNA, 5 ml of LB culture were grown overnight and 1 ml of cells was pelleted in a 1.5 ml tube. The cells were resuspended in 50 µl of water and were heated at 95° C. for 5 minutes to lyse the cells. The debris was pelleted and 10 µg of genomic DNA was used as a template in the PCR reaction.

For the PCR reaction, the primers were resuspended in MilliQ water at a concentration of 100 µM. The primers were then diluted in sterile water to 2 µM. The 50 µl PCR reaction mixture contained the following: 10×Pfu Buffer (5 µl), 10 mM dNTP (1 µl), BGUS forward and reverse primers at 2 µM (2 µl), *L. brevis* DNA at 0.5 µg/µL (1 µl), Pfu enzyme (Agilent Technologies Cat. No. 600136) at 2.5 U/µL (1 µl) and MilliQ Water (40 µl). The PCR program used for DNA amplification was as follows: 95° C./5 minutes, 40 cycles of 95° C./30 seconds, 50° C./30 seconds, 72° C./2.5 minutes, followed by 72° C./5 minutes, 4° C./00.

Production of the desired PCR product was confirmed by running 5 µL of the PCR reaction on a 1% agarose/TAE gel. The OMEGA-BioTek cycle pure kit (Cat. No. D6493-01) was used to remove the PCR reagents and the purified PCR product DNA was purified in 40 µL of elution buffer provided with the kit.

After amplification, the PCR product was digested with NdeI and HindIII for cloning into a bacterial expression vector. The reaction mixture contained the following: PCR product (16 µl), NdeI (NEB Cat. No. R0111S) (20 U/µl) (1 µl), HindIII (NEB Cat. No. R0104S) (20 U/µl) (1 µl), 10×NEB Reaction Buffer 2 (2 µl). The restriction enzyme digestion reaction was carried out at 37° C. for 60 minutes. The sample was then run on a 1% agarose/1×TAE gel and the band containing the *L. brevis* BGUS gene was excised.

The isolated *L. brevis* BGUS gene was then cloned into the pET28a(+) expression vector that had been cut with NdeI and HindIII and treated with shrimp alkaline phosphatase (SAP) (USB Cat No. 70092Y/Z/X). The ligation reaction contained: pET28a(+)/NdeI/HindIII/SAP (2 µL), BGUS ORF/NdeI/HindIII (8 µl), 10×NEB T4 DNA Ligase Buffer (5 µl), T4 DNA Ligase (NEB Cat. No. M0202S) (400 U/µl)(1 µl), water (34 µl). The ligation reaction mixture was incubated at room temperature overnight.

Following the overnight ligation reaction, the T4 DNA ligase was heat inactivated by heating the reaction at 68° C. for 10 minutes. For transformation into competent cells, an aliquot of competent DH5a cells was thawed on ice and 150 µl of the competent cells as added to the ligation reaction and mixed by gentle pipetting. The cells were then incubated on ice for 30 minutes, followed by heat shock at 42° C. for 3 minutes. The cells were then placed back on ice for 2 minutes and then transferred to 1 ml of LB medium in a 14 ml culture tube. The cell culture was incubated at 37° C. for 60 minutes at 250 rpm. Aliquots of the cells were added to LB-Kanamycin plates and grown overnight at 37° C. Colonies were picked for plasmid extraction and analysis by DNA sequencing using standard techniques to identify a plasmid that contained the cloned *L. brevis* strain 269Y wild type BGUS gene. The nucleotide sequence of the *L. brevis* strain 269Y wild type BGUS gene is shown in SEQ ID NO: 1 and the encoded amino acid sequence of the wild type *L. brevis* strain 269Y wild type BGUS enzyme is shown in SEQ ID NO: 2.

The amino acid sequence of the *L. brevis* strain 269Y wild type BGUS enzyme (SEQ ID NO: 2) was aligned with the amino acid sequence of the *L. brevis* strain RO1 wild type BGUS enzyme (SEQ ID NO: 5) to compare the two sequences. The alignment is shown in FIG. 1. The comparison showed that the *L. brevis* strain 269Y BGUS sequence has four amino acid differences as compared to the *L. brevis* strain RO1 BGUS sequence, at amino acid position 226 (isoleucine in strain 269Y; valine in strain RO1), amino acid position 272 (alanine in strain 269Y; threonine in strain RO1), amino acid position 447 (tyrosine in strain 269Y; serine in strain RO1) and amino acid position 568 (valine in strain 269Y; glycine in strain RO1).

Example 2: Mutagenesis of *L. brevis* Strain 269Y β-Glucuronidase (BGUS) Gene

The wildtype LbGUS strain 269Y gene was mutated using Q5® Site-Directed Mutagenesis Kit (New England Biolabs, USA) according to the manufacturer's instructions. Three mutants were prepared: The Lb1F mutant had a G564S single amino acid substitution. The nucleotide sequence encoding the Lb1F mutant is shown in SEQ ID NO: 6 and the encoded amino acid sequence is shown in SEQ ID NO: 7. The Lb-1C mutant had a single cysteine residue added to the C-terminal end of the enzyme. The nucleotide sequence encoding the Lb-1C mutant is shown in SEQ ID NO: 8 and the encoded amino acid sequence is shown in SEQ ID NO: 9. The Lb1F-1C mutant combined both the G564S substitution and the C-terminal cysteine residue addition. The nucleotide sequence encoding the Lb1F-1C mutant is shown in SEQ ID NO: 10 and the encoded amino acid sequence is shown in SEQ ID NO: 11.

To prepare the Lb1F and Lb-1C mutants, mutagenic primers were used for the whole LbGUS plasmid amplification. The following primers were used:

```
Lb1F Forward:
                              (SEQ ID NO: 12)
5'-AGCATTCAACGCGTTCAAGGAAATAA-3'

Lb1F Reverse:
                              (SEQ ID NO: 13)
5'-AAATTTTGTTTGGAAATCAGCAAAAT-3'

Lb-1C Forward:
                              (SEQ ID NO: 14)
5'-TGCTAGAAGCTTGCGGCCGCACTCGAG-3'

Lb-1C Reverse:
                              (SEQ ID NO: 15)
5'-TTTTTTATAATTAAAGTCCGGAATATTC-3'
```

To prepare the Lb1F-1C combination mutant, site-directed mutagenesis was performed using Lb1F specific primers shown above to amplify the whole Lb-1C plasmid. Subsequently, PCR products were subject to kinase-ligase-DpnI enzyme mix treatment for circularization and template removal. The mutant plasmids were transformed into NEB 5-alpha Competent *E. coli*. The LbGUS mutants were confirmed by sequencing.

Example 3: β-Glucuronidase Enzymatic Activity Assay

In this example, a standard enzyme activity assay for BGUS is described. The standard reporting format for this assay is in Units/ml for liquid formulations or in Units/mg for lyophilized formulations.

An activity assay buffer, 20 mM potassium phosphate buffer, pH 6.8, was prepared. The substrate solution used was 1 mM phenolphthaleine-glucuronide (PT-gluc) in water, prepared fresh. 400 µl of activity buffer was pipetted into a clean 1.5 ml microfuge tube. 4 µl of enzyme solution was added to the buffer to achieve a 1:100 or 1:200 dilution of the enzyme. Then, 30 µl of the diluted enzyme solution was pipetted in each well of a 96-well plate, with each enzyme solution performed in triplicate. 30 µl of diluted control enzyme solution was pipetted into control wells in triplicate. 30 µl of the PT-gluc substrate solution was pipetted into the wells with the enzyme solution. The plates were incubated for 30 minutes at 25° C. 180 µl of glycine was added to stop the reaction and develop color in each well. The absorbance at 540 nm was measured by standard methods.

1 Unit of BGUS activity is defined as an amount of enzyme that liberates 1 µg of phenolphthalein from phenolphthalein-glucuronide in 1 hour. Thus, to determine Units/ml of enzyme, first a standard curve was prepared by plotting background-subtracted absorbance at 540 nm for the phenolphthalein (PT) standards. Assuming a linear plot for the standard curve, the formula for determining the concentration of PT liberated by the enzyme is as follows:

[conc. PT in µg]=[(corrected absorbance at 540 nm)−(y intercept value)]/slope

The specific activity of the enzyme was determined by correcting for time and dilution factors, divided by the volume of enzyme used. Thus, to calculate the specific activity in Units/ml using the assay protocol above, the following formula was used:

Units/mL=(µg of PT released)×2×100/0.03 or 200/ 0.03 depending on dilution factor

Example 4: Enzymatic Activity of *L. brevis* Strain 269Y β-Glucuronidase Mutants In this example, the enzymatic assay of the *L. brevis* strain 269Y BGUS mutants was examined in a series of experiments comparing their activity at different pHs to wild type *L. brevis* stain 269Y BGUS enzyme activity. Enzymatic activity assays were carried out for 30 minutes at 25° C. To compare activity at different pHs, Reactions were carried out in: (i) 20 mM potassium phosphate buffer, pH 6.8; (ii) 0.1 M sodium acetate buffer, pH 5.2; and (iii) 0.1 M sodium acetate buffer, pH 4.5.

The results are shown in FIG. 3 and summarized in Table 1 below.

TABLE 1

Enzymatic Activity of *L. brevis* Strain 269Y Mutants at Different pHs

| pH | Enzyme | Enzyme Activity (KU/mg) |
|---|---|---|
| pH 6.8 | LbGUS | 50.98 |
| | Lb1F | 41.94 |
| | Lb-1C | 64.06 |
| | Lb1F-1C | 41.43 |
| pH 5.2 | LbGUS | 37.97 |
| | Lb1F | 74.74 |
| | Lb-1C | 67.25 |
| | Lb1F-1C | 83.23 |
| pH 4.5 | LbGUS | 16.24 |
| | Lb1F | 45.17 |
| | Lb-1C | 36.66 |
| | Lb1F-1C | 70.42 |

The results demonstrate that both the G564S substitution and the C-terminal cysteine addition, either alone or in combination, impart enhanced enzymatic activity to the *L. brevis* strain 269Y BGUS enzyme at low pH (e.g., below pH 6.8, such as at pH 5.2 and pH 4.5).

Example 5: Thermostability of *L. brevis* Strain 269Y β-Glucuronidase Mutants To examine the heat stability of the mutants, the mutant and wild-type enzymes were either unheated, or heated for 30 minutes at 55° C. or 65° C., and the enzyme activity was measured at each temperature. The results are summarized below in Table 2:

TABLE 2

Thermostability of *L. brevis* Strain 269Y Mutants at Different Temperatures

| Temperature | Enzyme | Enzyme Activity Before Heating (kU/mg) | Enzyme Activity Before Heating (kU/mg) |
|---|---|---|---|
| 55° C. | LbGUS | 36.74 | 22.82 |
| | Lb1F | 59.84 | 56.38 |
| | Lb-1C | 68.83 | 64.55 |
| | Lb1F-1C | 76.10 | 76.95 |
| 65° C. | LbGUS | 35.59 | 2.15 |
| | Lb1F | 71.39 | 71.79 |
| | Lb-1C | 68.89 | 5.54 |
| | Lb1F-1C | 76.60 | 69.54 |

The results showed that at 65° C. the G564S substitution imparted enhanced thermostability to the *L. brevis* strain 269Y BGUS enzyme and at 55° C. both the G564S substitution and the C-terminal cysteine addition, either alone or in combination, impart enhanced thermostability to the *L. brevis* strain 269Y BGUS enzyme.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
|---|---|
| 1 | *L. brevis* strain 269Y BGUS wild type nucleic acid sequence<br>ATGTTATATCCAATGGAAACAGCGTCACGAGTGGTTTTAGATTT<br>ATCAGGTGTCTGGCGGTTTATGATTGATAAAGAACAGATACCAG<br>TTGATGTGACTCGTCCGTTGCCGGCAACCTTATCGATGGCAGTT<br>CCAGCTTCATTTAACGATCAGACGGCATCAAAAGAGATCCGTGA<br>ACATGTCGGATACGTTTGGTATGAACGGTGTTTTGAGCTGCCCC<br>AATTACTGCGGCAAGAAAGACTCGTTTTGCGGTTTGGCTCCGCA<br>ACGCATGAGGCCTGGGTGTATCTTAATGGCCACTTAATCACGCA<br>TCACAAGGGTGGCTTTACACCGTTTGAAGTAGAAATTAATGACG<br>ACTTAGTGACTGGTGAGAATCGACTGACGGTTAAACTTAGTAAT<br>ATGCTTGACTATACAACTTTGCCGGTCGGACATTACAAAGAAAC<br>GCAAAATGAGACGGGCCAACGGGTACGGCAATTAGATGAAATT<br>TTGACTTCTTTAATTATGCGGGGTTACAGCGTCCTGTAAAAATC<br>TACAGTACGCCACACAGCTATATTCGAGACATTACGTTGACGCC<br>TAAGGTTAATTTGACCAATCACTCGGCGGTGGTTAATGGTGAAA<br>TTGAGACGGTAGGCGATGTTGAACAGGTAGTCGTCACGATCTTA<br>GACGAAGATAACCAGATTGTTGGTACCACGAGTGGGAAAACACT<br>GGCAATTGAGTTGAACTCAGTTCATCTATGGCAGCCGGGAAAGG<br>CCTACCTGTATCGCGCTAAAGTAGAATTGTATCAGGCGGGGCAA<br>GTGATTGATACGTACATCGAGGCGTTTGGCATTCGGCAAATTGC<br>GGTCAAGGCTGGTAAATTTTTGATTAACGGGCAGCCCTTTTACT<br>TCAAAGGATTTGGGAAACACGAAGACGCTTATATTCATGGTCGA<br>GGGTTAAGCGAACCACAGAATGTCTTGGATTTGAGCCTAATGAA<br>GCAGATGGGGGCTAATTCATTCCGAACGTCCCATTACCCGTATT<br>CAGAAGAAATGATGCGGCTATGTGATCGTGAGGGGATCGTTGTG<br>ATTGATGAGGTGCCGGCAGTTGGATTGATGCTGTCCTTTACCTT<br>TGATGTTTCGGCACTAGAAAAGGATGATTTTGAAGACGATACGT<br>GGGAAAAATTACGGACGGCTGAGGCCCATCGTCAGGCGATCACT<br>GAGATGATTGATCGTGATAAAAATCATGCCTCAGTGGTGATGTG<br>GTCAATCTCTAATGAGGCCGCCAACTTTTCCAAGGGGCCTATG<br>AGTACTTTAAGCCGTTATTTGATCTGGCTCGCAAGCTGGATCCA<br>CAGCAACGACCATGCACGTATACCAGTATTATGATGACAACGTT<br>AAAAACAGATCGGTGTTTGGCACTAGCCGATGTGATTGCGCTGA<br>ACCGATACTATGGTTGGTATATGGGCAATGGTGATTTGAAAGCA<br>GCAGAAACTGCGACGCGCGAAGAACTTTTAGCTTATCAGGCAAA<br>GTTCCCAGACAAGCCAATCATGTATACCGAATATGGTGCGGATA<br>CGATTGCGGGGTTGCATAGTAATTACGATGAGCCGTTTTCCGAA<br>GAGTTCCAAGAAGATTACTATCGGATGTGTAGTCGGGTTTTTGA<br>TGAAGTGACTAACTTTGTTGGCGAGCAACTTTGGAATTTTGCTG<br>ATTTCCAAACAAAATTTGGGATTCAACGCGTTCAAGGAAATAAG<br>AAGGGGATTTTTACCCGAGCGCGTGAACCCAAAATGGTGGTTCG<br>GTATTTAACACAACGGTGGCGGAATATTCCGGACTTTAATTATA<br>AAAAATAG |
| 2 | *L. brevis* strain 269Y BGUS wild type amino acid sequence<br>MLYPMETASRVVLDLSGVWRFMIDKEQIPVDVTRPLPATLSMAV<br>PASFNDQTASKEIREHVGYVWYERCFELPQLLRQERLVLRFGSA<br>THEAWVYLNGHLITHHKGGFTPFEVEINDDLVTGENRLTVKLSN<br>MLDYTTLPVGHYKETQNETGQRVRQLDENFDFFNYAGLQRPVKI<br>YSTPHSYIRDITLTPKVNLTNHSAVVNGEIETVGDVEQVVVTIL<br>DEDNQIVGTTSGKTLAIELNSVHLWQPGKAYLYRAKVELYQAGQ<br>VIDTYIEAFGIRQIAVKAGKFLINGQPFYFKGFGKHEDAYIHGR<br>GLSEPQNVLDLSLMKQMGANSFRTSHYPYSEEMMRLCDREGIVV<br>IDEVPAVGLMLSFTFDVSALEKDDFEDDTWEKLRTAEAHRQAIT<br>EMIDRDKNHASVVMWSISNEAANFSKGAYEYFKPLFDLARKLDP<br>QQRPCTYTSIMMTTLKTDRCLALADVIALNRYYGWYMGNGDLKA<br>AETATREELLAYQAKFPDKPIMYTEYGADTIAGLHSNYDEPFSE<br>EFQEDYYRMCSRVFDEVTNFVGEQLWNFADFQTKFGIQRVQGNK<br>KGIFTRAREPKMVVRYLTQRWRNIPDFNYKK |
| 3 | gagagacatatgttatatccaatggaaacag |
| 4 | gagagaaagcttctattattataattaaagtccggaatattc |
| 5 | *L. brevis* strain R01 BGUS wild type amino acid sequence (shown in FIG. 1) |
| 6 | *L. brevis* strain 269Y BGUS Lb1F mutant nucleotide sequence<br>ATGTTATATCCAATGGAAACAGCGTCACGAGTGGTTTTAGATTT<br>ATCAGGTGTCTGGCGGTTTATGATTGATAAAGAACAGATACCAG<br>TTGATGTGACTCGTCCGTTGCCGGCAACCTTATCGATGGCAGTT<br>CCAGCTTCATTTAACGATCAGACGGCATCAAAAGAGATCCGTGA<br>ACATGTCGGATACGTTTGGTATGAACGGTGTTTTGAGCTGCCCC<br>AATTACTGCGGCAAGAAAGACTCGTTTTGCGGTTTGGCTCCGCA<br>ACGCATGAGGCCTGGGTGTATCTTAATGGCCACTTAATCACGCA<br>TCACAAGGGTGGCTTTACACCGTTTGAAGTAGAAATTAATGACG<br>ACTTAGTGACTGGTGAGAATCGACTGACGGTTAAACTTAGTAAT<br>ATGCTTGACTATACAACTTTGCCGGTCGGACATTACAAAGAAAC<br>GCAAAATGAGACGGGCCAACGGGTACGGCAATTAGATGAAATT<br>TTGACTTCTTTAATTATGCGGGGTTACAGCGTCCTGTAAAAATC<br>TACAGTACGCCACACAGCTATATTCGAGACATTACGTTGACGCC<br>TAAGGTTAATTTGACCAATCACTCGGCGGTGGTTAATGGTGAAA<br>TTGAGACGGTAGGCGATGTTGAACAGGTAGTCGTCACGATCTTA<br>GACGAAGATAACCAGATTGTTGGTACCACGAGTGGGAAAACACT<br>GGCAATTGAGTTGAACTCAGTTCATCTATGGCAGCCGGGAAAGG<br>CCTACCTGTATCGCGCTAAAGTAGAATTGTATCAGGCGGGGCAA<br>GTGATTGATACGTACATCGAGGCGTTTGGCATTCGGCAAATTGC<br>GGTCAAGGCTGGTAAATTTTTGATTAACGGGCAGCCCTTTTACT<br>TCAAAGGATTTGGGAAACACGAAGACGCTTATATTCATGGTCGA<br>GGGTTAAGCGAACCACAGAATGTCTTGGATTTGAGCCTAATGAA<br>GCAGATGGGGGCTAATTCATTCCGAACGTCCCATTACCCGTATT<br>CAGAAGAAATGATGCGGCTATGTGATCGTGAGGGGATCGTTGTG<br>ATTGATGAGGTGCCGGCAGTTGGATTGATGCTGTCCTTTACCTT<br>TGATGTTTCGGCACTAGAAAAGGATGATTTTGAAGACGATACGT<br>GGGAAAAATTACGGACGGCTGAGGCCCATCGTCAGGCGATCACT<br>GAGATGATTGATCGTGATAAAAATCATGCCTCAGTGGTGATGTG<br>GTCAATCTCTAATGAGGCCGCCAACTTTTCCAAGGGGCCTATG<br>AGTACTTTAAGCCGTTATTTGATCTGGCTCGCAAGCTGGATCCA<br>CAGCAACGACCATGCACGTATACCAGTATTATGATGACAACGTT<br>AAAAACAGATCGGTGTTTGGCACTAGCCGATGTGATTGCGCTGA<br>ACCGATACTATGGTTGGTATATGGGCAATGGTGATTTGAAAGCA<br>GCAGAAACTGCGACGCGCGAAGAACTTTTAGCTTATCAGGCAAA<br>GTTCCCAGACAAGCCAATCATGTATACCGAATATGGTGCGGATA<br>CGATTGCGGGGTTGCATAGTAATTACGATGAGCCGTTTTCCGAA<br>GAGTTCCAAGAAGATTACTATCGGATGTGTAGTCGGGTTTTTGA<br>TGAAGTGACTAACTTTGTTGGCGAGCAACTTTGGAATTTTGCTG<br>ATTTCCAAACAAAATTTAGCATTCAACGCGTTCAAGGAAATAAG |

SUMMARY OF SEQUENCE LISTING

| SEQ ID NO: | DESCRIPTION |
|---|---|
| | AAGGGGATTTTTACCCGAGCGCGTGAACCCAAAATGGTGGTTCG<br>GTATTTAACACAACGGTGGCGGAATATTCCGGACTTTAATTATA<br>AAAAATAG |
| 7 | *L. brevis* strain 269Y BGUS Lb1F mutant amino acid sequence<br>MLYPMETASRVVLDLSGVWRFMIDKEQIPVDVTRPLPATLSMAV<br>PASFNDQTASKEIREHVGYVWYERCFELPQLLRQERLVLRFGSA<br>THEAWVYLNGHLITHHKGGFTPFEVEINDDLVTGENRLTVKLSN<br>MLDYTTLPVGHYKETQNETGQRVRQLDENFDFFNYAGLQRPVKI<br>YSTPHSYIRDITLTPKVNLTNHSAVVNGEIETVGDVEQVVVTIL<br>DEDNQIVGTTSGKTLAIELNSVHLWQPGKAYLYRAKVELYQAGQ<br>VIDTYIEAFGIRQIAVKAGKFLINGQPFYFKGFGKHEDAYIHGR<br>GLSEPQNVLDLSLMKQMGANSFRTSHYPYSEEMMRLCDREGIVV<br>IDEVPAVGLMLSFTFDVSALEKDDFEDDTWEKLRTAEAHRQAIT<br>EMIDRDKNHASVVMWSISNEAANFSKGAYEYFKPLFDLARKLDP<br>QQRPCTYTSIMMTTLKTDRCLALADVIALNRYYGWYMGNGDLKA<br>AETATREELLAYQAKFPDKPIMYTEYGADTIAGLHSNYDEPFSE<br>EFQEDYYRMCSRVFDEVTNFVGEQLWNFADFQTKFSIQRVQGNK<br>KGIFTRAREPKMVVRYLTQRWRNIPDFNYKK |
| 8 | *L. brevis* strain 269Y BGUS Lb-1C mutant nucleotide sequence<br>ATGTTATATCCAATGGAAACAGCGTCACGAGTGGTTTTAGATTT<br>ATCAGGTGTCTGGCGGTTTATGATTGATAAAGAACAGATACCAG<br>TTGATGTGACTCGTCCGTTGCCGGCAACCTTATCGATGGCAGTT<br>CCAGCTTCATTTAACGATCAGACGGCATCAAAAGAGATCCGTGA<br>ACATGTCGGATACGTTTGGTATGAACGGTGTTTTGAGCTGCCCC<br>AATTACTGCGGCAAGAAAGACTCGTTTTGCGGTTTGGCTCCGCA<br>ACGCATGAGGCCTGGGTGTATCTTAATGGCCACTTAATCACGCA<br>TCACAAGGGTGGCTTTACACCGTTTGAAGTAGAAATTAATGACG<br>ACTTAGTGACTGGTGAGAATCGACTGACGGTTAAACTTAGTAAT<br>ATGCTTGACTATACAACTTTGCCGGTCGGACATTACAAAGAAAC<br>GCAAAATGAGACGGGCCAACGGGTACGGCAATTAGATGAAAATT<br>TTGACTTCTTTAATTATGCGGGGTTACAGCGTCCTGTAAAAATC<br>TACAGTACGCCACACAGCTATATTCGAGACATTACGTTGACGCC<br>TAAGGTTAATTTGACCAATCACTCGGCGGTGGTTAATGGTGAAA<br>TTGAGACGGTAGGCGATGTTAACAGGTAGTCGTCACGATCTTA<br>GACGAAGATAACCAGATTGTTGGTACCACGAGTGGGAAAACACT<br>GGCAATTGAGTTGAACTCAGTTCATCTATGGCAGCCGGGAAAGG<br>CCTACCTGTATCGCGCTAAAGTAGAATTGTATCAGGCGGGGCAA<br>GTGATTGATACGTACATCGAGGCGTTTGGCATTCGGCAAATTGC<br>GGTCAAGGCTGGTAAATTTTTGATTAACGGGCAGCCCTTTTACT<br>TCAAAGGATTTGGGAAACACGAAGACGCTTATATTCATGGTCGA<br>GGGTTAAGCGAACCACAGAATGTCTTGGATTTGAGCCTAATGAA<br>GCAGATGGGGGCTAATTCATTCCGAACGTCCCATTACCCGTATT<br>CAGAAGAAATGATGCGGCTATGTGATCGTGAGGGGATCGTTGTG<br>ATTGATGAGGTGCCGGCAGTTGGATTGATGCTGTCCTTTACCTT<br>TGATGTTTCGGCACTAGAAAAGGATGATTTTGAAGACGATACGT<br>GGGAAAAATTACGGACGGCTGAGGCCCATCGTCAGGCGATCACT<br>GAGATGATTGATCGTGATAAAAATCATGCCTCAGTGGTGATGTG<br>GTCAATCTCTAATGAGGCCGCCAACTTTTCCAAGGGGGCCTATG<br>AGTACTTTAAGCCGTTATTTGATCTGGCTCGCAAGCTGGATCCA<br>CAGCAACGACCATGCACGTATACCAGTATTATGATGACAACGTT<br>AAAAACAGATCGGTGTTTGGCACTAGCCGATGTGATTGCGCTGA<br>ACCGATACTATGGTTGGTATATGGGCAATGGTGATTTGAAAGCA<br>GCAGAAACTGCGACGCGCGAAGAACTTTTAGCTTATCAGGCAAA<br>GTTCCCAGACAAGCCAATCATGTATACCGAATATGGTCGGATA<br>CGATTGCGGGGTTGCATAGTAATTACGATGAGCCGTTTTCCGAA<br>GAGTTCCAAGAAGATTACTATCGGATGTGTAGTCGGGTTTTTGA<br>TGAAGTGACTAACTTTGTTGGCGAGCAACTTTGGAATTTTGCTG<br>ATTTCCAAACAAAATTTAGCATTCAACGCGTTCAAGGAAATAAG<br>AAGGGGATTTTTACCCGAGCGCGTGAACCCAAAATGGTGGTTCG<br>GTATTTAACACAACGGTGGCGGAATATTCCGGACTTTAATTATA<br>AAAAATGCTAG |
| 9 | *L. brevis* strain 269Y BGUS Lb-1C mutant amino acid sequence<br>MLYPMETASRVVLDLSGVWRFMIDKEQIPVDVTRPLPATLSMAV<br>PASFNDQTASKEIREHVGYVWYERCFELPQLLRQERLVLRFGSA<br>THEAWVYLNGHLITHHKGGFTPFEVEINDDLVTGENRLTVKLSN<br>MLDYTTLPVGHYKETQNETGQRVRQLDENFDFFNYAGLQRPVKI<br>YSTPHSYIRDITLTPKVNLTNHSAVVNGEIETVGDVEQVVVTIL<br>DEDNQIVGTTSGKTLAIELNSVHLWQPGKAYLYRAKVELYQAGQ<br>VIDTYIEAFGIRQIAVKAGKFLINGQPFYFKGFGKHEDAYIHGR<br>GLSEPQNVLDLSLMKQMGANSFRTSHYPYSEEMMRLCDREGIVV<br>IDEVPAVGLMLSFTFDVSALEKDDFEDDTWEKLRTAEAHRQAIT<br>EMIDRDKNHASVVMWSISNEAANFSKGAYEYFKPLFDLARKLDP<br>QQRPCTYTSIMMTTLKTDRCLALADVIALNRYYGWYMGNGDLKA<br>AETATREELLAYQAKFPDKPIMYTEYGADTIAGLHSNYDEPFSE<br>EFQEDYYRMCSRVFDEVTNFVGEQLWNFADFQTKFSIQRVQGNK<br>KGIFTRAREPKMVVRYLTQRWRNIPDFNYKKC |
| 10 | *L. brevis* strain 269Y BGUS Lb1F-1C mutant nucleotide sequence<br>ATGTTATATCCAATGGAAACAGCGTCACGAGTGGTTTTAGATTT<br>ATCAGGTGTCTGGCGGTTTATGATTGATAAAGAACAGATACCAG<br>TTGATGTGACTCGTCCGTTGCCGGCAACCTTATCGATGGCAGTT<br>CCAGCTTCATTTAACGATCAGACGGCATCAAAAGAGATCCGTGA<br>ACATGTCGGATACGTTTGGTATGAACGGTGTTTTGAGCTGCCCC<br>AATTACTGCGGCAAGAAAGACTCGTTTTGCGGTTTGGCTCCGCA<br>ACGCATGAGGCCTGGGTGTATCTTAATGGCCACTTAATCACGCA<br>TCACAAGGGTGCTTTACACCGTTTGAAGTAGAAATTAATGACG<br>ACTTAGTGACTGGTGAGAATCGACTGACGGTTAAACTTAGTAAT<br>ATGCTTGACTATACAACTTTGCCGGTCGGACATTACAAAGAAAC<br>GCAAAATGAGACGGGCCAACGGGTACGGCAATTAGATGAAAATT<br>TTGACTTCTTTAATTATGCGGGGTTACAGCGTCCTGTAAAAATC<br>TACAGTACGCCACACAGCTATATTCGAGACATTACGTTGACGCC<br>TAAGGTTAATTTGACCAATCACTCGGCGGTGGTTAATGGTGAAA<br>TTGAGACGGTAGGCGATGTTAACAGGTAGTCGTCACGATCTTA<br>GACGAAGATAACCAGATTGTTGGTACCACGAGTGGGAAAACACT<br>GGCAATTGAGTTGAACTCAGTTCATCTATGGCAGCCGGGAAAGG<br>CCTACCTGTATCGCGCTAAAGTAGAATTGTATCAGGCGGGGCAA<br>GTGATTGATACGTACATCGAGGCGTTTGGCATTCGGCAAATTGC<br>GGTCAAGGCTGGTAAATTTTTGATTAACGGGCAGCCCTTTTACT<br>TCAAAGGATTTGGGAAACACGAAGACGCTTATATTCATGGTCGA<br>GGGTTAAGCGAACCACAGAATGTCTTGGATTTGAGCCTAATGAA<br>GCAGATGGGGGCTAATTCATTCCGAACGTCCCATTACCCGTATT<br>CAGAAGAAATGATGCGGCTATGTGATCGTGAGGGGATCGTTGTG<br>ATTGATGAGGTGCCGGCAGTTGGATTGATGCTGTCCTTTACCTT<br>TGATGTTTCGGCACTAGAAAAGGATGATTTTGAAGACGATACGT<br>GGGAAAAATTACGGACGGCTGAGGCCCATCGTCAGGCGATCACT<br>GAGATGATTGATCGTGATAAAAATCATGCCTCAGTGGTGATGTG<br>GTCAATCTCTAATGAGGCCGCCAACTTTTCCAAGGGGGCCTATG<br>AGTACTTTAAGCCGTTATTTGATCTGGCTCGCAAGCTGGATCCA<br>CAGCAACGACCATGCACGTATACCAGTATTATGATGACAACGTT<br>AAAAACAGATCGGTGTTTGGCACTAGCCGATGTGATTGCGCTGA<br>ACCGATACTATGGTTGGTATATGGGCAATGGTGATTTGAAAGCA<br>GCAGAAACTGCGACGCGCGAAGAACTTTTAGCTTATCAGGCAAA<br>GTTCCCAGACAAGCCAATCATGTATACCGAATATGGTCGGATA<br>CGATTGCGGGGTTGCATAGTAATTACGATGAGCCGTTTTCCGAA<br>GAGTTCCAAGAAGATTACTATCGGATGTGTAGTCGGGTTTTTGA<br>TGAAGTGACTAACTTTGTTGGCGAGCAACTTTGGAATTTTGCTG<br>ATTTCCAAACAAAATTTAGCATTCAACGCGTTCAAGGAAATAAG<br>AAGGGGATTTTTACCCGAGCGCGTGAACCCAAAATGGTGGTTCG<br>GTATTTAACACAACGGTGGCGGAATATTCCGGACTTTAATTATA<br>AAAAATGCTAG |
| 11 | *L. brevis* strain 269Y BGUS Lb1F-1C mutant amino acid sequence<br>MLYPMETASRVVLDLSGVWRFMIDKEQIPVDVTRPLPATLSMAV<br>PASFNDQTASKEIREHVGYVWYERCFELPQLLRQERLVLRFGSA<br>THEAWVYLNGHLITHHKGGFTPFEVEINDDLVTGENRLTVKLSN<br>MLDYTTLPVGHYKETQNETGQRVRQLDENFDFFNYAGLQRPVKI<br>YSTPHSYIRDITLTPKVNLTNHSAVVNGEIETVGDVEQVVVTIL<br>DEDNQIVGTTSGKTLAIELNSVHLWQPGKAYLYRAKVELYQAGQ<br>VIDTYIEAFGIRQIAVKAGKFLINGQPFYFKGFGKHEDAYIHGR<br>GLSEPQNVLDLSLMKQMGANSFRTSHYPYSEEMMRLCDREGIVV<br>IDEVPAVGLMLSFTFDVSALEKDDFEDDTWEKLRTAEAHRQAIT<br>EMIDRDKNHASVVMWSISNEAANFSKGAYEYFKPLFDLARKLDP<br>QQRPCTYTSIMMTTLKTDRCLALADVIALNRYYGWYMGNGDLKA<br>AETATREELLAYQAKFPDKPIMYTEYGADTIAGLHSNYDEPFSE<br>EFQEDYYRMCSRVFDEVTNFVGEQLWNFADFQTKFSIQRVQGNK<br>KGIFTRAREPKMVVRYLTQRWRNIPDFNYKKC |

SUMMARY OF SEQUENCE LISTING

| SEQ ID NO: | DESCRIPTION |
|---|---|
| 12 | Lb1F Forward Primer sequence<br>AGCATTCAACGCGTTCAAGGAAATAA |
| 13 | Lb1F Reverse Primer sequence<br>AAATTTTGTTTGGAAATCAGCAAAAT |
| 14 | Lb-1C Forward Primer sequence<br>TGCTAGAAGCTTGCGGCCGCACTCGAG |
| 15 | Lb-1C Reverse Primer sequence<br>TTTTTTATAATTAAAGTCCGGAATATTC |
| 16 | $Xaa_{0-8}$-Cys-$Xaa_{0-2}$, wherein Xaa = any amino acid |
| 17 | Gly-Leu-Cys-Gly-Arg |

The invention claimed is:

1. A mutated *Lactobacillus brevis* strain 269Y β-glucuronidase (LbGUS) enzyme consisting of the amino acid sequence shown in SEQ ID NO: 2, wherein G564 in SEQ ID NO: 2 is substituted with an amino acid comprising a side chain comprising a non-aromatic hydroxyl group or histidine or asparagine.

2. The mutated LbGUS enzyme of claim 1, wherein G564 in SEQ ID NO: 2 is substituted with serine.

3. The mutated LbGUS enzyme of claim 1, wherein G564 in SEQ ID NO: 2 is substituted with threonine.

4. The mutated LbGUS enzyme of claim 1, which has the amino acid sequence shown in SEQ ID NO: 7.

5. The mutated LbGUS enzyme of claim 4, which is encoded by the nucleotide sequence shown in SEQ ID NO: 6.

6. A mutated *Lactobacillus brevis* strain 269Y β-glucuronidase (LbGUS) enzyme consisting of the amino acid sequence shown in SEQ ID NO: 2, wherein:
   (i) G564 in SEQ ID NO: 2 is substituted with an amino acid comprising a side chain comprising a non-aromatic hydroxyl group or histidine or asparagine; and
   (ii) a cysteine residue is appended at or near the carboxy terminus of the enzyme, wherein the carboxy terminus has the sequence: $Xaa_{0.8}$-Cys-$Xaa_{0.2}$, wherein Xaa=any amino acid (SEQ ID NO: 16).

7. The mutated LbGUS enzyme of claim 6, wherein G564 in SEQ ID NO: 2 is substituted with serine.

8. The mutated LbGUS enzyme of claim 6, wherein G564 in SEQ ID NO: 2 is substituted with threonine.

9. The mutated LbGUS enzyme of claim 6, which has the amino acid sequence shown in SEQ ID NO: 11.

10. The mutated LbGUS enzyme of claim 9, which is encoded by the nucleotide sequence shown in SEQ ID NO: 10.

11. A packaged formulation comprising a container comprising a preparation of the mutated LbGUS enzyme of claim 1, which has an enzymatic activity of at least 5,000 Units/ml or 5,000 Units/mg.

12. The packaged formulation of claim 11, which is an aqueous solution with an enzymatic activity of at least 50,000 Units/ml.

13. The packaged formulation of claim 11, which is a lyophilized preparation with an enzymatic activity of at least 50,000 Units/mg.

14. The packaged formulation of claim 11, wherein the preparation is stable at least six months at 2-8° C.

15. The packaged formulation of claim 11, wherein the preparation lacks detectable sulfatase activity.

16. The mutated LbGUS enzyme of claim 1, wherein G564 in SEQ ID NO: 2 is substituted with histidine.

17. The mutated LbGUS enzyme of claim 1, wherein G564 in SEQ ID NO: 2 is substituted with asparagine.

18. The mutated LbGUS enzyme of claim 6, wherein G564 in SEQ ID NO: 2 is substituted with histidine.

19. The mutated LbGUS enzyme of claim 6, wherein G564 in SEQ ID NO: 2 is substituted with asparagine.

20. A packaged formulation comprising a container comprising a preparation of the mutated LbGUS enzyme of claim 6, which has an enzymatic activity of at least 5,000 Units/ml or 5,000 Units/mg.

21. The packaged formulation of claim 20, which is an aqueous solution with an enzymatic activity of at least 50,000 Units/ml.

22. The packaged formulation of claim 20, which is a lyophilized preparation with an enzymatic activity of at least 50,000 Units/mg.

23. The packaged formulation of claim 20, wherein the preparation is stable at least six months at 2-8° C.

24. The packaged formulation of claim 20, wherein the preparation lacks detectable sulfatase activity.

* * * * *